United States Patent
Jooris et al.

(10) Patent No.: US 12,383,187 B2
(45) Date of Patent: Aug. 12, 2025

(54) METHOD AND SYSTEM FOR MONITORING A LEVEL OF NON-PHARMACOLOGICALLY-INDUCED MODIFIED STATE OF CONSCIOUSNESS

(71) Applicant: HypnoVR, Lampertheim (FR)

(72) Inventors: Diane Jooris, Tervuren (BE); Mario Huyghe, Desselgem (BE); Clémence Toussaint, Oteppe (BE)

(73) Assignee: HYPNOVR, Lampertheim (FR)

(*) Notice: Subject to any disclaimer, the term of this patent is extended or adjusted under 35 U.S.C. 154(b) by 328 days.

(21) Appl. No.: 17/429,373

(22) PCT Filed: Feb. 7, 2020

(86) PCT No.: PCT/EP2020/053136
§ 371 (c)(1),
(2) Date: Aug. 9, 2021

(87) PCT Pub. No.: WO2020/165042
PCT Pub. Date: Aug. 20, 2020

(65) Prior Publication Data
US 2022/0104751 A1    Apr. 7, 2022

(30) Foreign Application Priority Data
Feb. 11, 2019   (EP) .................................... 19156346

(51) Int. Cl.
*A61B 5/374* (2021.01)
*A61B 3/113* (2006.01)
(Continued)

(52) U.S. Cl.
CPC .............. *A61B 5/374* (2021.01); *A61B 5/291* (2021.01); *A61B 5/4821* (2013.01);
(Continued)

(58) Field of Classification Search
CPC ........... A61B 5/291; A61B 5/31; A61B 5/369; A61B 5/4812; A61B 5/4806;
(Continued)

(56) References Cited

U.S. PATENT DOCUMENTS

| 6,434,419 B1 * | 8/2002 | Gevins | ................... G16H 50/20 600/544 |
| 2007/0010723 A1 * | 1/2007 | Uutela | ................. A61B 5/0205 128/920 |

(Continued)

FOREIGN PATENT DOCUMENTS

| CN | 109224243 A | 1/2019 |
| WO | 2016044944 A1 | 3/2016 |
| WO | 2018129211 A1 | 7/2018 |

OTHER PUBLICATIONS

PCT International Search Report dated May 6, 2020 in connection with PCT/EP2020/053136.
(Continued)

*Primary Examiner* — Carrie R Dorna
*Assistant Examiner* — Joshua Daryl D Lannu
(74) *Attorney, Agent, or Firm* — Maier & Maier, PLLC

(57) ABSTRACT

A computer-implemented method for determining and/or monitoring a level of modified state of consciousness of a subject receiving a treatment session comprising modifying the state of consciousness of the subject non-pharmacologically, the method comprising the steps of: receiving response data representing a subject's response to the treatment session, wherein the response data comprises measured data comprising electroencephalogram, EEG, data, the EEG data comprising: data collected from at least one of: at least one frontal (F) EEG electrode located on the scalp anatomical region corresponding to a frontal lobe of the subject, and at least one parietal (P) EEG electrode located on the scalp anatomical region corresponding to a parietal lobe of the
(Continued)

subject, determining from the response data, the level of modified state of consciousness of a subject of the subject.

18 Claims, 10 Drawing Sheets

(51) Int. Cl.

| | |
|---|---|
| A61B 5/00 | (2006.01) |
| A61B 5/024 | (2006.01) |
| A61B 5/0532 | (2021.01) |
| A61B 5/08 | (2006.01) |
| A61B 5/11 | (2006.01) |
| A61B 5/1455 | (2006.01) |
| A61B 5/16 | (2006.01) |
| A61B 5/256 | (2021.01) |
| A61B 5/291 | (2021.01) |
| A61B 5/316 | (2021.01) |
| A61B 5/389 | (2021.01) |
| A61B 5/398 | (2021.01) |
| A61M 21/00 | (2006.01) |
| A61M 21/02 | (2006.01) |
| G16H 20/40 | (2018.01) |
| G16H 20/70 | (2018.01) |
| G16H 40/63 | (2018.01) |
| G16H 50/30 | (2018.01) |

(52) U.S. Cl.
CPC ............ *A61B 5/6803* (2013.01); *A61B 5/743* (2013.01); *G16H 50/30* (2018.01); *A61B 5/02438* (2013.01); *A61B 5/1114* (2013.01); *A61B 5/14551* (2013.01); *A61B 5/389* (2021.01); *A61B 5/398* (2021.01)

(58) Field of Classification Search
CPC ..... A61B 5/4821; A61B 5/374; A61B 5/6803; A61B 5/743; A61B 5/02438; A61B 5/1114; A61B 5/14551; A61B 5/389; A61B 5/398; A61B 5/316; A61B 5/4848; A61B 3/113; A61B 5/024; A61B 5/0532; A61B 5/08; A61B 5/16; A61B 5/256; G16H 50/30; G16H 20/40; G16H 20/70; G16H 40/63; A61M 21/02; A61M 2021/0077; A61M 2230/04; A61M 2230/10
See application file for complete search history.

(56) References Cited

U.S. PATENT DOCUMENTS

| | | | | |
|---|---|---|---|---|
| 2010/0010289 | A1* | 1/2010 | Clare | A61B 5/16 600/27 |
| 2014/0081094 | A1* | 3/2014 | Jordan | A61B 5/725 600/383 |
| 2015/0190086 | A1* | 7/2015 | Chan | A61B 5/4812 600/300 |
| 2015/0208940 | A1* | 7/2015 | Addison | A61B 5/7257 600/300 |
| 2018/0361110 | A1* | 12/2018 | Garcia Molina | A61B 5/38 |
| 2019/0126033 | A1* | 5/2019 | Pradeep | A61B 5/4812 |

OTHER PUBLICATIONS

PCT Written Opinion of the International Searching Authority Report dated May 6, 2020 in connection with PCT/EP2020/053136.
PCT Third Party Observation dated Jun. 10, 2021 in connection with in connection with PCT/EP2020/053136.
Fingelkurts, Andrew A. et al.: "Cortex functional connectivity as a neurophysiological correlate of hypnosis: An EEG case study", Neuropsychologia, vol. 45, No. 7, Jan. 17, 2007 (Jan. 17, 2007), pp. 1452-1462, XP005736619.
Panda, Rajanikant et al.: "Neural correlates of modified subjective state of consciousness induced by hypnosis using EEG-connectivity approach", Belgian Brain Congress 2018—Belgian Brain Council, Jan. 17, 2019 (Jan. 17, 2019), XP055688200.
Terhune, Devin Blair et al.: Differential frontal-parietal phase synchrony during hypnosis as a function of hypnotic suggestibility, Psychophysiology, 48, (2011), 1444-1447.
White, David et al.: EEG Correlates of Virtual Reality Hypnosis, Intl. Journal of Clinical and Experimental Hypnosis, 57(1):94-116, 2009.
European Patent Office, "Communication", issued in European Patent Application No. 20 702 184.1, which is a counterpart to U.S. Appl. No. 17/429,373, issued on Dec. 12, 2022, 7 pages.
Jose Leon-Carrion et al., "Delta-alpha ratio correlates with level of recovery after neurorehabilitation in patients with acquired brain injury", Clinical Neurophysiology, vol. 120, No. 6, Jun. 1, 2009, pp. 1039-1045, XP026146275, ISSN: 1388-2457, https://doi.org/10.1016/j.clinph.2009.01.021.

* cited by examiner

METHOD AND SYSTEM FOR MONITORING A LEVEL OF NON-PHARMACOLOGICALLY-INDUCED MODIFIED STATE OF CONSCIOUSNESS

CROSS-REFERENCE TO RELATED APPLICATIONS

This application is a U.S. national stage entry under 35 U.S.C. § 371 of PCT International Patent Application No. PCT/EP2020/053136, filed Feb. 7, 2020, which claims priority to European Patent Application No. 19156346.9, filed Feb. 11, 2019, the contents of each of which are incorporated herein by reference in their entirety.

FIELD OF THE INVENTION

The present invention is in a field of monitoring of a modified state of consciousness of a subject under non-pharmacological optionally with pharmacological (i.e. mixed)—influence, and provision of a standardised measurement.

BACKGROUND TO THE INVENTION

Despite existence of non-pharmacological solutions (e.g. clinical hypnosis), healthcare providers mostly deliver pharmacological solutions (e.g. benzodiazepines, opioids) to provide patient sedation for creating a state of calm and managing pain and anxiety.

Pharmacological sedation presents risks, which are incremental in presence of several factors such as age, respiratory or cardiac pathologies, obesity. Excessive sedation used (conscious/unconscious sedation, general anesthesia) through drugs increase the risk/incidence of moderate to severe adverse events. Monitoring systems (such as Bis and Entropy) are designed for pharmacological sedation Non-pharmacological sedation has been practiced for decades (hypnosedation/clinical hypnosis/hypnotherapy) using hypnosis delivered one-on-one or via playback of recorded session, optionally with locoregional anesthesia (LRA) if needed for conscious IV sedation. Monitoring systems for pharmacological sedation poorly correlate with clinical parameters of depth of dominantly non-pharmacologically induced sedation/anesthesia. Changes in brain activity in hypnotic state have been objectivized by brain imagery (fMRI and/or EEG), but so far no objective quantification has been available to measure, objectivate and, based on these, manage patient's hypnotic or dissociation state. The hypnotic state has never been objectively quantified. There is no existing way to quantify patient's physiological/psychological level of dissociation in a hypnotic state/modified state of consciousness. No current way to objectively monitor/trend/assess/predict procedural/surgical amnesia and patient's level of dissociation.

There exists in the art a need for measuring a modified state of consciousness of a subject in order to arrive at a standard scale or index, useful for an assessment of the subject by a medical practitioner or carer.

SUMMARY

Provided herein is a computer-implemented method for determining and/or monitoring a level of modified state of consciousness of a subject receiving a treatment session comprising modifying the state of consciousness of the subject non-pharmacologically, the method comprising the steps of:
  receiving response data representing a subject's response to the treatment session, wherein the response data comprises measured data comprising electroencephalogram, EEG, data, the EEG data comprising:
    data collected from at least one of:
      at least one frontal (F) EEG electrode located on the scalp anatomical region corresponding to a frontal lobe of the subject, and
      at least one parietal (P) EEG electrode located on the scalp anatomical region corresponding to a parietal lobe of the subject,
  determining from the response data, the level of modified state of consciousness of a subject of the subject.

The EEG data may comprises data collected from the at least one F-EEG electrode, and optionally the at least one P-EEG electrode, and the determining comprises:
  extracting from the at least one F-EEG electrode data, a power, F-power, associated with a band in a delta-theta, dt, frequency range;
  and optionally extracting from the at least one P-EEG electrode data, a power, P-power, associated with a band in the delta-theta, dt, frequency range;
  wherein the dt frequency range frequencies in a range encompassing both delta and theta brain waves;
  wherein the F-power associated with a band in the dt frequency range and optionally P-power associated with a band in the dt frequency range are indicative of the level of non-pharmacologically modified state of consciousness of the subject.

The F-power may be associated with a frequency range greater than 0 Hz and equal to or less than 8 Hz, or a band within the aforementioned frequency range. The P-power may be associated with a frequency range greater than 0 Hz and equal to or less than 8 Hz, or a band within the aforementioned frequency range. A reduction of said F-power associated with a band in the dt frequency range, and optionally a reduction of said P-power associated with a band in the dt frequency range, may be indicative of a lowered level of non-pharmacologically modified state of consciousness of the subject.

The EEG data may comprise data collected from the at least one F-EEG electrode and the determining comprises extracting from the F-EEG electrode data, a mean signal peak-to-peak amplitude, F-MSPA, wherein the F-MSPA is indicative of the level of non-pharmacologically modified state of consciousness of the subject. A reduction of said F-MSPA may be indicative of a lowered level of non-pharmacologically modified state of consciousness of the subject.

A depth of dissociation, DoD, of the subject may be determined from:
  the F-power associated with a band in the dt frequency range, and optionally the P-power associated with a band in the dt frequency range as defined in herein,
  and optionally the F-MSPA as defined herein, and
  the DoD is used to determine the level of non-pharmacologically modified state of consciousness of the subject.

The level of modified state of consciousness may be of a subject whose level of consciousness will be/is being non-pharmacologically-modified and optionally pharmacologically-modified.

The method may further comprise determining from the response data, a depth of state index, DoSI, the DoSI representing a measure of the non-pharmacologically-optionally with the pharmacologically-modified (mixed) state of consciousness of the subject.

The method may further comprise determining from the response data, a depth of hypnosis index, DoHI, the DoHI representing a measure of the non-pharmacologically-modified state of consciousness of the subject.

The method may further comprise determining from the response data, a depth of dissociation index, DoDI, the DoDI representing a measure of the non-pharmacologically-modified state of consciousness of the subject.

The method may be for determining a level of sedation of a subject induced non-pharmacologically and optionally non-pharmacologically.

The method may further comprise providing an output to a graphical user interface, GUI, indicating numerically and/or graphically one or more of:

current DoS(I) and/or DoH(I) and/or DoD(l);
current ratio between two of DoS(I), DoH(l), DoD(l);
trending (historical) DoS(I) and/or DoH(I) and/or DoD(l);
expected DoS(I) and/or DoH(I) and/or DoD(I);
and optionally one or more current data components, preferably one or more EEG data components.

Further provided is a system for determining and/or monitoring the level of consciousness of the subject receiving the treatment session, the system comprising:

a monitoring apparatus configured to obtain response data comprising measured data of the subject during the treatment session;
a controller module configured for receiving measured data from the monitoring apparatus,
optionally a media renderer configured for presenting the treatment session to the subject for non-pharmacologically modifying the level of consciousness of the subject
wherein the monitoring apparatus comprises, for obtaining measured data of the subject during the treatment session, one or more of:
a frontal (F) EEG electrode configured for collection of F-EEG electrode data from the scalp anatomical region corresponding to a frontal lobe of the subject,
a parietal (P) EEG electrode configured for collection of P-EEG electrode data from the scalp anatomical region corresponding to a parietal lobe of the subject,
and wherein the controller module is configured to determine from the response data, the level of modified consciousness of the subject during the treatment session.

The system may be configured to carry out a method described herein.

Provided is a method for determining and/or monitoring a level of non-pharmacologically-optionally with a pharmacologically-modified state of consciousness of a subject receiving a treatment session, the method comprising the steps of:

receiving response data representing a subject's response to the treatment session;
transforming the response data into a depth of state (DoS) index (DoSI) and/or a depth of hypnosis (DoH) index (DoHI), the DoHI and/or DoSI representing a measure of the non-pharmacologically-optionally with the pharmacologically-modified (mixed) state of consciousness of the subject.

The response data may comprise measured data and/or observational data and/or self-reported data, preferably measured data, wherein:

the measured data is data measured from the subject using a device and comprises one or more of electrical activity data, physiological data, motion-tracking data, facial expression data
the observational data is data observed or provided about the subject by another person or by a database, and comprises one or more of subject's movements/lack of movement, procedural events, clinical observation (skin color, groaning or verbalization of discomfort . . . ),—age, surgery type, ethnic origin, language, dosages of sedation drugs;
the self-reported is data reported by the subject, and comprises one or more of level of dissociation during treatment, estimated duration of the procedure, recall of the events during the session.

The electrical activity data may comprise electroencephalogram (EEG) data and optionally electromyography (EMG) data, electrodermal activity (EDA) data, electrocardiogram (ECG) data.

The response data may be transformed into the DoSI and/or DoHI using an evaluation protocol, the evaluation protocol comprise use of one or more of a mathematical (e.g. statistical) model, trained machine-leaning model, mathematical index, reference data.

The evaluation protocol may weigh data components of the response data equally or differently, optionally wherein data components having a high relevance and precision are accorded a higher weighting.

The evaluation protocol may be refined comprising:
receiving response data representing a subject's response to the treatment session,
receiving independently measured data of the DoSI and/or DoHI
using the response data and independently measured data to refine the evaluation protocol.

The method may further comprise a step of determining an expected DoSI and/or DoHI for a point in time of the treatment session based on position in a hypnotic treatment session and/or population data The method may further comprise providing an output to a graphical user interface, GUI, indicating numerically and/or graphically one or more of:

current DoSI and/or DoHI;
current ratio between two DoSI and DoHI;
trending (historical) DoSI and/or DoHI;
trending (historical) ratio between DoSI and DoHI;
expected DoSI and/or DoHI; and
expected ratio between DoSI and DoHI.
and optionally one or more current data components, preferably one or more of EEG data, EMG data, and pulse rate data,
and optionally one or more derived indexes wherein a derived index is an index derived from one or more data components and/or from DoSI and/or from DoHI.

Further provided is a system for determining and/or monitoring a level of non-pharmacological and/or pharmacological modified state of consciousness of a subject receiving a treatment session, the system comprising:

media renderer configured for presenting the treatment session to the subject;
a monitoring apparatus configured to obtained measured data of the subject;
a controller module configured for receiving measured data from the monitoring apparatus, and transforming the response data comprising the measured data into a depth of state (DoS) index (DoSI) and/or a depth of hypnosis (DoH) index (DoHI), the DoHI and/or DoSI representing a measure of the non-pharmacological and/or pharmacological modified state of consciousness of the subject.

The monitoring apparatus may comprise one or more of:

an electroencephalogram (EEG) capturing unit comprising at least two (e.g. 2, 3, 4, 5 or more) electrodes for acquiring electrical activity data from the subject brain, and for outputting an EEG data component of the measured data;

an electromyography (EMG) capturing unit comprising at least one (e.g. 1,2, 3, 4, 5 or more) electrode for acquiring electrical activity data from the subject muscle tissue, and for outputting an EMG data component of the measured data;

an electrodermal activity (EDA) capturing unit comprising at least one (e.g. 1, 2, 3, 4, 5 or more) electrode for acquiring electrical activity data from the subject skin, and for outputting an EDA data component of the measured data; an electrocardiogram (ECG) comprising at least one (e.g. 1, 2, 3, 4, 5 or more) for acquiring electrical activity data from the subject heart, and for outputting an ECG data component of the measured data;

a heart rate monitoring unit comprising at least one sensor (e.g. 1, 2, 3, 4, 5 or more) or electrode for acquiring data from the subject heart, and for outputting an heart rate data component of the measured data;

a physiological monitoring unit comprising at least one (e.g. 1, 2, 3, 4 or more) sensor for acquiring subject's physiological data, such as one or more of pulse rate, heart rate variation, blood pressure, respiration rate, brain oxygenation, blood $O_2$ saturation, regional and/or central blood $O_2$ saturation, skin conductance, body temperature, and outputting a physiological data component of the measured data;

a body motion tracking unit may comprise at least one (e.g. 1, 2, 3, 4 or more) motion sensor for acquiring subject's body motion such as movements of the head, limb (arms, legs, hands, knee, elbow), and outputting a body motion tracking data component of the measured data;

an eye-tracking unit may comprise at least one (e.g. 1, 2, 3, 4 or more) camera for monitoring movement of one or both eyes of the subject, and outputting eye tracking data component of the measured data;

a facial expression capturing unit may comprise at least one (e.g. 1, 2, 3, 4 or more) camera for monitoring facial expressions of the subject, and outputting facial expression data component of the measured data.

The media renderer may comprise a screen and/or sound transducer for presenting a treatment session that contains hypnosis and/or other evidence-based psychological and/or mind/body intervention to the subject.

The media renderer and one or more electrodes and/or one more sensors, and/or one more cameras of the monitoring apparatus may be integrated into a wearable device.

The one or more electrodes and/or one more sensors, and/or one more cameras of the monitoring apparatus may be integrated into a strap or face mask of the wearable device.

The system may further comprise a graphical user interface, GUI, configured to indicate numerically and/or graphically one or more of:
current DoSI and/or DoHI;
current ratio between two DoSI and DoHI;
trending (historical) DoSI and/or DoHI;
trending (historical) ratio between DoSI and DoHI;
expected DoSI and/or DoHI; and
expected ratio between DoSI and DoHI.
and optionally one or more current data components, preferably one or more of EEG data, EMG data, and pulse rate data
and optionally one or more derived indexes wherein a derived index is an index derived from one or more data components and/or from DoSI and/or from DoHI.

Further provided is a computing device or system configured for performing the method described herein, and/or
a computer program or computer program product having instructions which when executed by a computing device or system cause the computing device or system to perform the method described herein, and/or
a computer readable medium having stored thereon instructions which when executed by a computing device or system cause the computing device or system to perform the method described herein, and/or
a data stream which is representative of a computer program or computer program product having instructions which when executed by a computing device or system cause the computing device or system to perform the method described herein.

FIGURE LEGENDS

Figure 13:
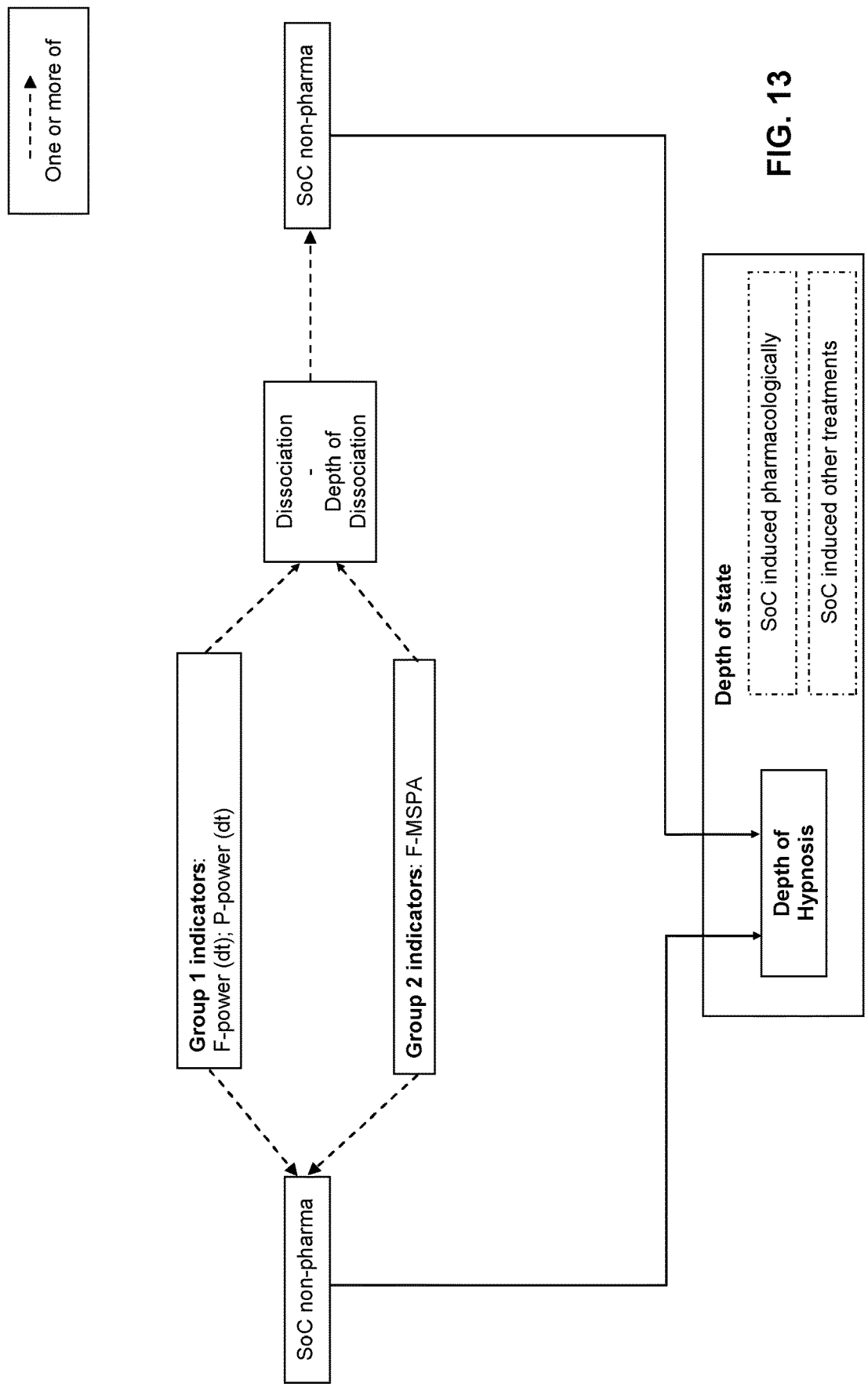

FIG. 13 is a schematic illustration of Groups 1 to 2 indicators extracted from response data. On the right is shown the link to Dissociation (and use to determination of Depth of Dissociation); this is linked to non-pharmacologically induced modified state of consciousness (SoC non-pharma). On the left is shown links between Groups 1 to 2 indicators and non-pharmacologically induced modified state of consciousness (SoC non-pharma). SoC non-pharma is linked to Depth of Hypnosis. Depth of State is linked to Depth of Hypnosis, optionally with a measure of the modified state of consciousness induced pharmacologically, and optionally with a measure of the modified state of consciousness induced by other treatments.

Figure 14:
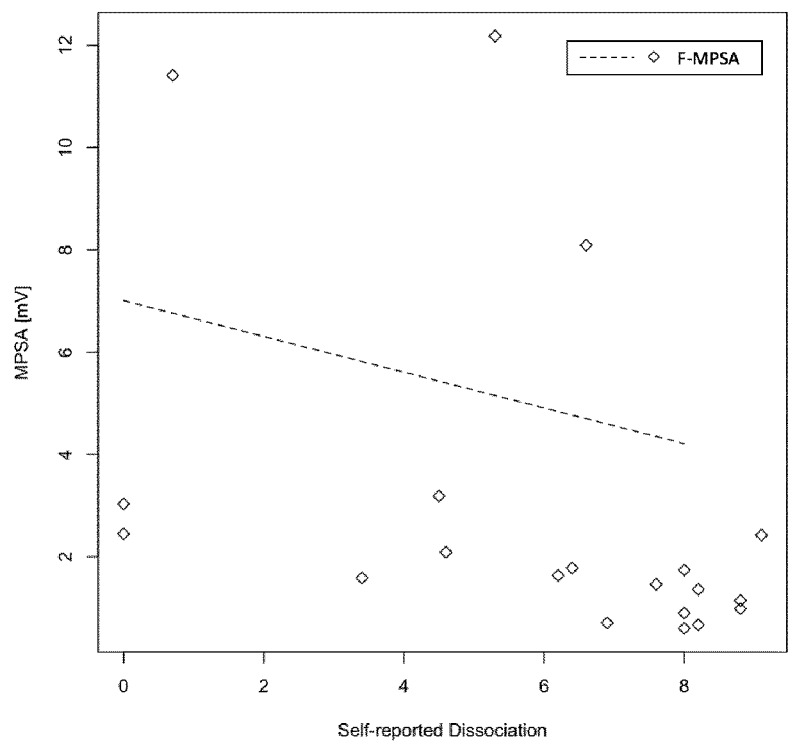

FIG. 14 is a graph indicating the correlation between MSPA measured at the EEG F-electrode and dissociation.

Figure 15:
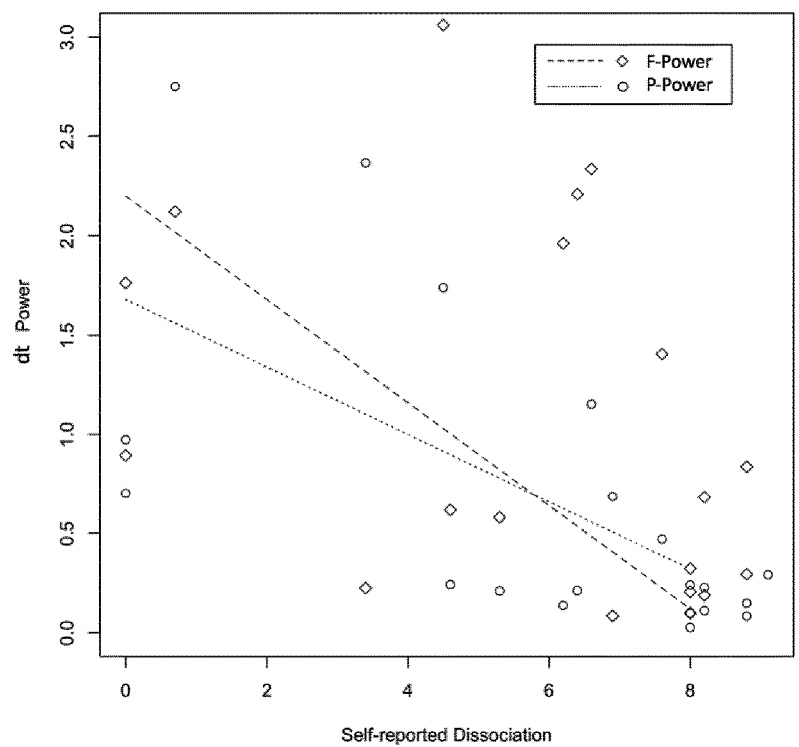

FIG. 15 is a graph indicating a correlation between self-reported dissociation and computed dt power at EEG electrodes F, P.

DETAILED DESCRIPTION

Before the present system and method of the invention are described, it is to be understood that this invention is not limited to particular systems and methods or combinations described, since such systems and methods and combinations may, of course, vary. It is also to be understood that the terminology used herein is not intended to be limiting, since the scope of the present invention will be limited only by the appended claims.

As used herein, the singular forms "a", "an", and "the" include both singular and plural referents unless the context clearly dictates otherwise.

The terms "comprising", "comprises' and "comprised of" as used herein are synonymous with "including", "includes" or "containing", "contains", and are inclusive or open-ended and do not exclude additional, non-recited members, elements or method steps. It will be appreciated that the terms "comprising", "comprises" and "comprised of" as used herein comprise the terms "consisting of", "consists" and "consists of".

The recitation of numerical ranges by endpoints includes all numbers and fractions subsumed within the respective ranges, as well as the recited endpoints.

The term "about" or "approximately" as used herein when referring to a measurable value such as a parameter, an amount, a temporal duration, and the like, is meant to encompass variations of +/−10% or less, preferably +/−5% or less, more preferably +/−1% or less, and still more preferably +/−0.1% or less of and from the specified value, insofar such variations are appropriate to perform in the disclosed invention. It is to be understood that the value to which the modifier "about" or "approximately" refers is itself also specifically, and preferably, disclosed.

Whereas the terms "one or more" or "at least one", such as one or more or at least one member(s) of a group of members, is clear per se, by means of further exemplification, the term encompasses inter alia a reference to any one of said members, or to any two or more of said members, such as, e.g., any ≥3, ≥4, ≥5, >6 or ≥7 etc. of said members, and up to all said members.

All references cited in the present specification are hereby incorporated by reference in their entirety. In particular, the teachings of all references herein specifically referred to are incorporated by reference.

Unless otherwise defined, all terms used in disclosing the invention, including technical and scientific terms, have the meaning as commonly understood by one of ordinary skill in the art to which this invention belongs. By means of further guidance, term definitions are included to better appreciate the teaching of the present invention.

In the following passages, different aspects of the invention are defined in more detail. Each aspect so defined may be combined with any other aspect or aspects unless clearly indicated to the contrary. In particular, any feature indicated as being preferred or advantageous may be combined with any other feature or features indicated as being preferred or advantageous.

Reference throughout this specification to "one embodiment" or "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to a person skilled in the art from this disclosure, in one or more embodiments. Furthermore, while some embodiments described herein include some but not other features included in other embodiments, combinations of features of different embodiments are meant to be within the scope of the invention, and form different embodiments, as would be understood by those in the art. For example, in the appended claims, any of the claimed embodiments can be used in any combination.

In the present description of the invention, reference is made to the accompanying drawings that form a part hereof, and in which are shown by way of illustration only of specific embodiments in which the invention may be practiced. Parenthesized or emboldened reference numerals affixed to respective elements merely exemplify the elements by way of example, with which it is not intended to limit the respective elements. It is to be understood that other embodiments may be utilised and structural or logical changes may be made without departing from the scope of the present invention. The following detailed description, therefore, is not to be taken in a limiting sense, and the scope of the present invention is defined by the appended claims.

Provided herein is a method for determining and/or monitoring a level of modified state of consciousness of a subject receiving a treatment session to modify the state of consciousness of the subject. The treatment session that modifies the state of consciousness of the subject may be non-pharmacological (e.g. hypnosis). The treatment session that modifies the state of consciousness of the subject may be non-pharmacological (e.g. hypnosis) and pharmacological (i.e. mixed treatment session). The method comprises the step of receiving response data representing a subject's response to the treatment session and determining from response data the level of modified state of consciousness of the subject. The level of modified state of consciousness is determined in real time.

The inventors have found that for the first time a strong association between response data in particular measured data collected from at least one of a frontal-EEG electrode, a parietal-EEG electrode and central-EEG electrode and the state of consciousness of the subject during a non-pharmacological treatment session to modify the state of consciousness of the subject. For the first time, an objective measure of a level of modified state of consciousness of the subject can be determined in real time in non-pharmacological hypnosis (which causes dissociation). This is applicable in many situations, for instance, when a subject is undergoing an intervention under non-pharmacological sedation. The intervention may be any including curative, and/or ameliorative, and/or diagnostic. The intervention may be invasive (e.g. surgical, endoscopic, catheterisation) or non-invasive (e.g. medical image acquisition, radiotherapy).

State of consciousness refers to a measurement of a subject self-awareness as well environmental awareness determining the subject's presence sensation, arousability (emotional response) and (physical) responsiveness to a stimulus or stimuli, characterized by modification of the physiological activity and by a neurological signature. The stimulus may be from the environment (e.g. an external event) and/or internal.

In a modified state of consciousness, i.e. where the level of consciousness is lowered, the subject is more relaxed, more dissociated is more prone to suggestions, and is optionally sedated to moderate or deep level. Subject's cognitive functions may be absorbed in a specific task, and brain processes which usually happen together are separated. Subject's physiology is usually modified (less involuntary movement i.e. swallowing, limb movement, eye blinking, higher stability of vital signs, larger respiratory patterns and improved oxygenation rates . . . ). In a modified state of consciousness, subject might experience partial or total catalepsy as well as disconnect from the environment (i.e. not hear/respond to verbal command). Senses may be under/overactivated according to requirements. A subject with a lower level of consciousness is able have an improved experience of an intervention. The intervention may be any including curative, and/or ameliorative, and/or diagnostic. The intervention may be invasive (e.g. surgical, endoscopic, catheterisation) or non-invasive (e.g. medical image acquisition, radiotherapy).

The state of consciousness induced non-pharmacologically can be determined from a depth of dissociation (DoD) of the subject during the treatment session as discussed later below.

A treatment session is applied to the subject to modify the state of consciousness of the subject. The treatment session may include one or more of hypnosis and/or other evidence-based psychological and/or mind/body intervention (i.e. non-pharmacological treatment), administration of active pharmacological ingredient (i.e. pharmacological treatment), other treatments (e.g. acupuncture, mechanical treatment, mindfulness, other non-pharmacological treatment). Preferably it comprises hypnosis; it has a known effect of dissociation. The degree to which the state of consciousness of the subject has been modified by hypnosis may be referred to as depth of hypnosis (DoH). The degree to which the state of consciousness of the subject has been modified by hypnosis and optionally by active pharmacological ingredient and optionally by other treatments may be referred to as depth of state (DoS).

In particular a non-pharmacological treatment includes mainly hypnosis but also other treatments which are used to potentialize the hypnosis session and/or improve dissociation/change of consciousness/therapeutic impact. Other non-pharmacological treatment session may include one or more of, acupuncture, tapping, electrical stimulation, mechanical treatment, mindfulness, eye movement desensitization and reprocessing (EMDR).

Example of pharmacological treatment session may administration of an anaesthetic. Examples of anaesthetics include:
An inhalation agent such as Desflurane, Enflurane, Halothane, Isoflurane, Methoxyflurane, Nitrous oxide, Sevoflurane (inhaled)
An intravenous agent such as Barbiturates, Amobarbital, Methohexital, Thiamylal, Thiopental, Benzodiazepines, Diazepam, Lorazepam, Midazolam, Etomidate, Ketamine, Propofol As used herein the term "subject" refers to the beneficiary of the therapeutic session. The "user" refers to a person or persons operating the method or system. The user may be a care provider such as a physician, or medical assistant, or non-medical assistant (e.g. friend, relative, helper) of the subject. In some circumstances, the user may be the subject, for instance, where a treatment is self-administered at home.

Hypnosis is one way of inducing an altered state of consciousness in a subject. The hypnosis therapy may be medical (clinical) hypnosis therapy, or home hypnosis therapy, or hypnosis therapy provided in any care or wellness environment. The hypnosis therapy may be extramural hypnosis therapy that is not provided in a care institution (i.e. not provided in a clinic, hospital, care centre). While immersed in the altered state of consciousness, the subject's self-perception and the peripheral awareness are affected, changing the subject's experience of his/her sensation, perception, and thoughts, and making the subject prone to follow suggestions. Subject is absorbed and dissociated from reality.

Figure 1:
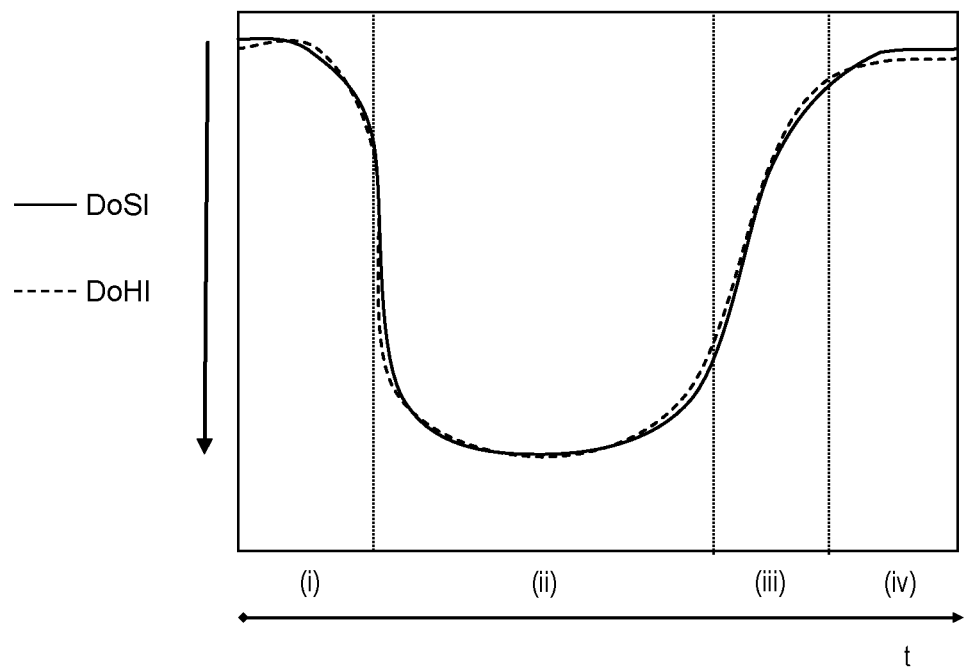
FIG. 1 shows an exemplary visualisation of an exemplary treatment session comprising four phases, as measured using DoSI and DoHI.

A hypnotic treatment session typically comprises 4 sequential phases as exemplified in FIG. 1, (i) an induction phase, (ii) a deepening phase, (iii) a transition phase, and/or (iv) a re-alerting phase. While immersed in the treatment sessions the subject's self-perception and the peripheral awareness are affected, the immersion depth increasing during the (i) phase and reaching a maximum during the (ii) phase. The subject becomes prone to suggestive control during the (ii) phase, during which time the subject may be sedated, induced to relax, etc. Afterwards the subject is returned to a normal state of a consciousness by passing the (iii) and (iv) phases.

The phases are described in detail below, namely:
(i) The induction phase, wherein the subject is prepared to be immersed into the altered state. In this phase the subject is typically provided with a feeling of comfort, safety and relaxation to the subject.
(ii) The deepening phase, wherein the subject is placed in an altered state of consciousness. This state is typically characterised by full or partial dissociation of reality and lack of or reduced movement unless expressly suggested in the therapy.
(iii) The transition phase, wherein the subject is exposed to suggestive information, which may aid in remembering or forgetting specific event of the therapy and/or to addressing one or more subject specific issues (also called post-hypnotic suggestions).
(iv) Re-alerting phase, wherein the subject is returned to a normal state of consciousness. In this phase the subject typically returns his/her senses and the dissociative state ends. This phase may be optional or part of the typical hypnotic treatment session.

The hypnotic treatment session may be delivered by a hypnotist or hypnotherapist, more preferably it is presented using a media renderer such as a virtual reality head set for an fully immersive effect as described below in more detail. A stored hypnotic treatment session may be played through the media renderer, the content of the treatment session specific to the treatment. The hypnotic session can be a self-hypnosis session.

While in the altered state of consciousness induced by hypnosis, the subject is more dissociated and can undergo interventions (e.g. invasive procedures) in the absence or with a lower dose of a pharmacological (anesthetic/analgesic/anxiolytic) agent.

The response data representing a subject's response to the treatment session is used to determine the state of consciousness of the subject, in particular a level or modified state of consciousness.

The response data may comprise measured data and optionally observational data and/or self-reported data. The response data may comprise measured data and/or observational data and/or self-reported data. The response data contains one or more data components, each component being derived from a single measurement (e.g. EEG, EMG, EDA, ECG, EOG), single observation (e.g. movement, skin colour), or single self-reported event as discussed later below.

Measured data is data obtained from the subject using one or more devices such as an electrode and/or sensor (e.g. transducer, camera, motion sensor) disposed in relation to the subject. Observational data is data obtained from a non-self (hetero) observation of the subject. Self-reported data is data or information reported by the subject during or after the treatment. The measured data may comprise one or more measured data components. (e.g. EEG is a measured data component).

The response data may comprise electrical activity data. Electrical activity data is measured data. Electrical activity data is any data derived from a measurement obtained by an electrical electrode. The electrode is typically placed on the skin. Usually the data is captured by at least 2 electrodes (e.g. 2, 3, 4, 5 or more). Examples of electrode-captured data include electroencephalogram (EEG) data, electromyography (EMG) data, electrodermal activity (EDA) data, electrocardiogram (ECG) data, electrooculogram (EOG) data. It is preferred that the response data comprises at least EEG data. Any electrical data component (e.g. EEG data) may or may not be processed prior to being used as response data.

The response data may comprise physiological data. Physiological data is measured data. Physiological data is data derived from a measurement on the subject obtained by a device usually containing a transducer, camera, motion sensor. Physiological data excludes the above-mentioned electrical activity data. Examples of physiological data include pulse rate data, heart rate data (e.g. heart rate, heart rate variation data), blood pressure data, respiratory (rate) data (e.g. respiratory rate, respiratory rate variation data), brain oxygenation data, blood $O_2$ saturation data, regional and/or central blood $O_2$ saturation data, skin conductance data, skin galvanic data (e.g. GSR (galvanic skin response) data), body temperature data, photoplethysmogram (PPG) data. Blood oxygen saturation may be, for instance $SpO_2$, $SvO_2$, and the like. Any physiological data component (e.g. pulse rate data) may or may not be processed prior to being used as response data.

The response data may comprise motion-tracking data. Motion-tracking data is measured data. The motion tracking data is data derived from a movement of the body or of a part of the body. Typically, motion tracking data is measured by one or more motion sensors (e.g. a 2- or 3-axis accelerometer, gyroscope, one or more cameras). The motion-tracking data may comprise body one or more of body tracking data (e.g. head, limb (arms legs hands), bodily shaking) and/or eye tracking data. The motion may be spontaneous and/or as a result of electrical stimulation.

The response data may comprise facial expression data. Facial-expression data is measured data. The facial expression data is data relating an emotions and/or nociception. Typically, facial expression data is measured by one or more cameras directed at the face (or EMG sensors).

The response data may comprise observational data. The observational data is data observed about the subject by another person. The observational data is data observed by the user (e.g. care provider such as a physician, or medical assistant, or non-medical assistant (e.g. friend, relative, helper)), or by a stakeholder associated with the user (e.g. hospital), or obtained from a database (e.g. medical records). The observed data may comprise one or more observed data components (e.g. a subject's movements is an observed data component). Observational data may include one or more of subject's movements/lack of movement; procedural events; clinical observation (skin color, groaning or verbalization of discomfort . . . ); age, type of surgery, interventional data, ethnic origin, language, other demographics; dosages of sedation and/or other drugs.

The response data may comprise self-reported data. The self-reported data is data reported by the subject. The self-reported data may be provided during the session. The self-reported data may be provided before, and/or during and/or after the treatment session. Preferably, the self-reported data is provided before and/or after the treatment session. The self-reported data may comprise one or more self-reported data components (e.g. level of dissociation during treatment is a self-reported data component). Self-reported data may include one or more of level of dissociation during treatment, overall comfort, estimated duration of the procedure, recall of the events during the session, and other related registrations.

Electroencephalography (EEG) is a technique well known in the art for recording electrical activity of the brain. Electrodes placed along the scalp as certain locations measure voltage fluctuations resulting from electrical impulse within the neurons of the brain (mainly of the cortex). It reflects how different neurons/populations of neurons in the brain networks communicate with each other from electrical impulse. Electroencephalography produces an electroencephalogram. The electroencephalogram EEG data may be refined to a particular electrode location, such as the frontal, parietal or central electrodes mentioned above. The EEG data may comprise a frequency-based parameter and/or a phase-based parameter, and/or amplitude-based parameter. Frequency-based parameter may be obtained by a frequency-based analysis of EEG signals. It may be used to measure the power contained in a specific signal frequency band, where power refers to a square of amplitude of the frequency domain signals typically within a specified in a frequency range (e.g. a band spanning or within delta-theta frequency range, or a band spanning or within theta-alpha frequency range).

The "delta-theta" (dt) frequency band refers to a band of frequencies in a range encompassing both delta and theta brain waves. The delta-theta (dt) range is typically greater than 0 Hz and equal to or less than 8 Hz. The theta brain waves are preferably slow theta brain waves (greater than 3 Hz and equal to or less than 6 Hz). The width of the delta-theta (dt) band may be at least 2 Hz. The width of the band may span the entire range of the delta-theta" (dt) frequency. Most preferably the delta-theta (dt) frequency band is greater than or equal to 1 Hz and less than or equal to 6 Hz.

The phase-based parameter may be obtained by phase-based analysis of EEG signals. The amplitude-based parameter may be obtained by amplitude-based analysis of EEG signals e.g. mean signal peak-to-peak amplitude (MSPA) in a time domain. The signal peak amplitude is the maximum excursion of the signal wave from the zero point. The signal peak-to-peak amplitude is the distance from a negative peak to a positive peak. EEG data may be acquired with one or more EEG electrodes placed on the scalp in the anatomical regions corresponding to the (positional) frontal lobe and the parietal lobe.

A frontal EEG electrode (F-EEG electrode) is located on the scalp anatomical region corresponding to the frontal lobe. It is configured for attachment to or contact with the scalp anatomical region corresponding to the frontal lobe. It records F-EEG electrode data. The frontal lobe refers to the anatomical part of the brain. The region of the frontal lobe may be along the sagittal plane, more preferable to in middle of the scalp anatomical region corresponding to the frontal lobe, along the sagittal plane. At least one F-EEG electrode may be provided or used.

The parietal EEG electrode (P-EEG electrode) is located on the scalp anatomical region corresponding to the parietal lobe. It is configured for attachment to or contact with the scalp anatomical region corresponding to the parietal lobe. It records P-EEG electrode data. The parietal lobe refers to the anatomical part of the brain. The region of the parietal lobe may be along the sagittal plane, more preferable to in middle of the scalp anatomical region corresponding to the parietal lobe, along the sagittal plane. At least one P-EEG electrode may be provided or used.

As a minimum one localised EEG electrode may be used (e.g. F-EEG electrode). However, it is understood that a second electrode (ground electrode) may be employed for common mode rejection, i.e. to dissociate relevant information from noise; this can be placed anywhere on the scalp, for instance in another region of the scalp, in a bilateral position. A third electrode (reference electrode) may be employed to compute voltage differences; this can be placed anywhere on the scalp, for instance at an electrically neutral location.

Heart rate data may be acquired using two or more electrocardiogram (ECG) electrodes placed on the skin using peripheral or precordial placement. ECG detects electrical activity of the heart. Alternatively or in addition, heart rate data may be acquired by another source, e.g. using a photoplethysmogram (PPG) sensor placed on the skin. PPG detects blood volume changes vasculature below the skin. Heart rate data may comprise heart rate, heart rate variability, derived metrics, phase-based parameters, frequency-based parameters.

Respiratory data may be acquired using one or more force/movement transducer (e.g. chest band) or air pressure sensor, or derived from a PPG sensor or ECG sensor. The respiratory data may comprise one or more of respiration rate, respiration rate variability (also known as respiration variability), inhalation pressure, exhalation pressure, respiratory rhythm, respiratory depth, respiratory pattern and derived indexes. Respiratory data may be known herein as respiratory rate data.

EMG data may be acquired using two or more EMG electrodes placed on the skin, preferably on limbs or face; or derived from another sensor like EEG. It represents electrical activity data from the subject muscle tissue. It may comprise a frequency-based parameter and/or a phase-based parameter and/or an amplitude-based parameter.

Electrooculogram (EOG) data may be acquired using two or more EOG electrodes placed on the skin around the eye (e.g. above and below, or to the left and right of the eye). EOG records eye movements based on the corneo-retinal standing potential that exists between the front and the back of the human eye. EOG data may comprise eye movements/fixation, eye blinks, synchronization of both eye's movements.

Skin galvanic data may be acquired using two or more conductance-measuring electrodes placed on the skin. The data represents skin conductivity and is linked to changes in sweat glands activity, that are reflective of sympathetic activity. Skin galvanic data may comprise conductivity variability, peak amplitude/latency, trends.

$SpO_2$ data is a measure of blood oxygen saturation. It may be measured using a number of techniques such as pulse oximetry. $SpO_2$ data may comprise timeline values. It is a key parameter for anesthesiologists since it is linked to respiratory function and it reflects tissue oxygenation.

The eye tracking data may include one or more of pupil dilation, eye fixation, blink rate or frequency, eye-EMG (EOG), eye movement, blink closing duration, blink flurries, eye closure rate, eyelid distance change (with respect to the normal eyelid distance). Pupil dilation can give information about the activity in the coeruleus, the main site of norepinephrine (stress hormones) synthesis in the brain, as well as the state of sleepiness/alertness.

The body motion tracking data (e.g. head, limb (arms legs hands)) may include an indication of increased or reduced body movement. A change in motion of the head may be a sign of lack of concentration in the tasks/low immersiveness/distraction during passive "deepening" phase of the treatment session.

The response data may comprise measured data that comprises EEG data, and EMG, and eye tracking data, observational data that comprises patient's observed movement or lack of movement and dosages of received medication and self-reported data that comprises dissociation rating. Preferably the response data comprises EEG data. Preferably the self-reported data (if any) comprises ratings for dissociation.

The response data may be used to determine a depth of dissociation (DoD) of the subject during the treatment session.

Depth of Dissociation (DoD) is degree to which the subject has the feeling of being present in an alternative reality, at the expense of the reality of his actual environment at a given time as well as degree to which the subject is disconnected from his sensory experience and sense of self. It is a direct indicator of the depth in which the subject is under hypnosis. In other words, it is a main contributor to the Depth of Hypnosis. At a neurophysiological level, dissociation is characterized by a reprioritization of mental processes, given a priority attention to an alternative reality. It may be used an indicator of the degree of inattention regarding stimuli coming from the actual environment and/or regarding internal event. As mentioned elsewhere herein, the depth of dissociation (DoD) of the subject may be determined from a Group 1 indicator and/or a Group 2 indicator. The DoD may be measured in respect of a non-pharmacological treatment session.

The response data or level of modified state of consciousness determined from the response data may be used to determine depth of state (DoS) and/or a depth of hypnosis (DoH). The depth of dissociation (DoD) determined from the response data may be used to determine depth of state (DoS) and/or a depth of hypnosis (DoH).

The DoH is the same as or indicative of the level of consciousness of the subject induced non-pharmacologically (e.g. by hypnosis). As previously explained in a modified state of consciousness, the subject is more relaxed and dissociated, and is less bothered by unpleasant events, is more prone to suggestions, and is optionally sedated. Subject's cognitive functions may be occupied in a specific task, and brain processes which usually happen together are separated. The creation of this dissociative state allows a reduced perception of peripheral stimuli and a subject's modified perception of the self and the self in the environment. Indicators that contribute to a DoH of a subject of include at least depth of dissociation (DoD) experienced by the subject. As mentioned elsewhere herein, a DoD may be determined from group 1 data and/or group 2 data.

The DoS is indicative of the level of consciousness of the subject induced non-pharmacologically (e.g. by hypnosis) and optionally pharmacologically. The DoS may be determined from different depths of state or different depth of state indexes. For example, the DoS may be the sum of different depths of state or different depth of state indexes.

The DoS may be determined from DoH and other contributions to the state such as by a pharmacological treatment. For example, the DoS may be the sum of different depths of state or different depth of state indexes. The DoS may be equal to DoH, particularly when treatment session contains only hypnosis.

The response data may comprise measured data comprising electroencephalography, EEG, data, the EEG data comprising:
data collected from at least one of:
a frontal EEG electrode (F-EEG electrode) located on the scalp anatomical region corresponding to a frontal lobe of the subject,
a parietal EEG electrode (P-EEG electrode) located on the scalp anatomical region corresponding to a parietal lobe of the subject,
determining from the response data, the level of modified state of consciousness of the subject.

There is preferably at least one F-EEG electrode and at least one P-EEG electrode.

The inventors have found a strong association between data collected from at least one of the F-EEG electrode, and P-EEG electrode and the level of modified state of consciousness of the subject. In particular, they can be used to indicate a depth of dissociation (DoD) of the subject. The DoD of a subject is linked to the state of consciousness of the subject. The DoD of a subject is also linked to a depth of hypnosis of the subject.

Preferably the EEG data comprises data collected from the F-EEG electrode, and optionally P-EEG electrode, and the determining comprises:
extracting from the F-EEG electrode data, a power associated with a band in the delta-theta, dt, frequency range (F-power (dt)); and
optionally extracting from the P-EEG electrode data, a power associated with a band in the delta-theta, dt, frequency range(P-power (dt));
wherein the F-power (dt and optionally P-power ((Group 1 indicators) are indicative of the state of consciousness of a subject. In particular, they are indicative of how dissociated the subject is. Dissociation is linked to the state of consciousness of a subject.

Preferably F-power(dt) is extracted from the frequency range greater than 0 Hz and equal to or less than 8 Hz, or from a narrower band therein. Preferably P-power(dt) is extracted from the frequency range greater than 0 Hz and equal to or less than 8 Hz, or from a narrower band therein. There is preferably at least one F-EEG electrode and at least one P-EEG electrode.

The Group 1 indicators F-power (dt), and optionally P-power (dt), are indicators of the state of consciousness of a subject. In particular, they are linked to how dissociated the subject is.

A change of said F-power (dt) and optionally of said P-power (dt) optionally compared with respective reference values is further indicative of the state of modified state of consciousness of a subject. In particular a reduction of said F-power (dt) and optionally of said P-power (dt) optionally compared with respective reference values is indicative a lower state of consciousness of a subject.

A reduction (drop) of said F-power (dt) and optionally of said P-power (dt) optionally compared with a respective reference value(s) is indicative of a more dissociated state.

Preferably the EEG data comprises data collected from the F-EEG electrode and from the P-EEG electrode, and the determining comprises extracting from the F-EEG electrode data, F-power (dt) and from the P—EEG electrode data P-power ($1dt$), wherein the combination of F-power (dt) and P-power (dt) are indicative of the state of consciousness of a subject.

Preferably the EEG data comprises data collected from the F-EEG electrode, and the determining comprises extracting from the F-EEG electrode data, a mean signal peak-to-peak amplitude (F-MSPA), wherein the F-MSPA (Group 2 indicator) is indicative of the state of consciousness of a subject. In particular, they are indicative of how dissociated the subject is. Dissociation is linked to the state of consciousness of a subject.

The Group 2 indicator F-MSPA is linked to the state of consciousness of a subject. In particular, it is linked to how dissociated the subject is.

A change of said F-MSPA compared with a reference value is further indicative of the level of modified state of consciousness of a subject. A reduction of said F-MSPA compared with a reference value is indicative of a reduced state of consciousness of a subject. A reduction of said F-MSPA compared with a respective reference value(s) is indicative of a more dissociated state.

A depth of dissociation (DoD) of the subject may be determined from the state of consciousness of a subject. The DoD is correlated with the state of consciousness of the subject. In particular, the depth of dissociation (DoD) may be determined from a Group 1 indicator and/or a Group 2 indicator.

In particular, the depth of dissociation (DoD) may be determined from:
the F-power (dt) and optionally the P-power (dt) (Group 1 indicator), and/or
the F-MSPA (Group 2 indicator).
Preferably, the DoD of the subject is determined from
the F-power (dt) and optionally P-power (dt) (Group 1 indicator), and
optionally F-MSPA (Group 2 indicator).
Preferably, the DoD of the subject is determined from
the F-power (dt) and optionally P-power (dt) (Group 1 indicator), and
F-MSPA (Group 2 indicator).

A depth of state (DoS) of the subject may be determined from the state of consciousness of a subject. A depth of state (DoS) of the subject may be determined from the DoD. A depth of state (DoS) of the subject may be determined from a Group 1 indicator and/or a Group 2 indicator.

A depth of hypnosis (DoH) of the subject may be determined from the state of consciousness of a subject. A depth of hypnosis (DoH) of the subject may be determined from the DoD. A depth of hypnosis (DoH) of the subject may be determined from a Group 1 indicator and/or a Group 2 indicator Described herein are one or more indexes, which are standardised indexes indicating the level or degree to which subject's state of consciousness has been modified by the treatment session. Typically an index is standardised or normalised as compared to a reference state.

Indexes described herein include depth of hypnosis index (DoHI), depth of state index (DoSI), depth of dissociation index (DoDI).

A depth of hypnosis index (DoHI) is a standardised index of the depth of hypnosis (DoH) indicating the level or degree to which the state of consciousness of the subject has been modified by the treatment session that is non-pharmacological (e.g. hypnotic), as compared to a reference state.

A depth of state index (DoSI) is a standardised index of the depth of state (DoS) indicating the level or degree to which the state of consciousness of the subject has been modified by the treatment session that is non-pharmacological (e.g. hypnotic) treatment session and optionally by a pharmacological, as compared to a reference state.

A depth of dissociation index (DoDI) is a standardised index of the depth of dissociation (DoD) indicating the level or degree to which dissociation of the subject has been modified by the treatment session, in particular by a non-pharmacological treatment session as compared to a reference state.

An index (e.g. one or more of DoHI, DoSI, DoDI) may have a scale with a first and a second limit. The first limit may represent no modified state of consciousness and the second limit may represent the deepest modified state of consciousness. The first limit may represent an initial (reference) state of the subject. The first limit may represent no/lightly modified state of consciousness and the second limit may represent a fully/deeply modified state of consciousness. The first limit may represent a light trance, and the second limit may represent a deep trance. The first and second limits may be numerically represented e.g. 0 to 20, 20 to 0, 0 to 60, 60 to 0, 0 to 100, 100 to 0, 0 to 1, 1 to 0 respectively. The second limit may be higher than the first limit, or the first limit may be higher than the second limit.

The choice of a higher number for the second limit may depend on the subject or user perspective. An anaesthetist may have a preference that the first limit is higher (e.g. 1, 60, 100, 100%) than the second limit (e.g. 0, 0%).

A subject with an index (especially DoSI, DoHI, DoDI) towards the second limit, for instance, can be safely operated on by surgery when the modified state of consciousness is for anaesthetic effect.

The index may have a scale between the first and second limits; the scale may be linear, logarithmic, or other. The scale may be continuous, categorical, discrete, percentage, ratio.

The index (e.g. one or more of DoHI, DoSI, DoDI) may be indicative of a number of different levels of consciousness, hypnosis (DoHI), state (DoSI), and dissociation (DoDI) for the subject. The number of levels may be any, for instance 3 to 10, preferably 4 to 8 levels. There may be 4, 6, or 8 levels. The levels may divided be within the first and second limits. The division may be even (linear), logarithmic, or according to another scheme. The lowest level (e.g. 1st level) may correlate with or contain the first limit, the highest level (e.g. 4th level) may correlate with or contain the second limit. When a index is a value between 100 (first limit) and 0 (second limit) and the number of levels is 4, the 4 levels may be 100-76 (1st level), 75 to 51 (2nd level), 50 to 26 (3rd level), 25 to 0 (4th level). It is appreciated that the end points of the levels may allow a continuous numerical scale (not interrupted) into the next level. When the index is a value between 100 (first limit) and 0 (second limit) and the number of levels is 8, the 8 levels may be 100-87.5 (1st level), 87.5 to 75 (2nd level), 75 to 62.5 (3rd level), 62.5 to 50 (4th level), 50 to 37.5 (5th level), 37.5 to 25 (6th level), 25 to 12.5 (7th level), 12.5 to 0 to (8th level). The skilled person would be able to determine the extent of the scale (e.g. 100 to 0, or 60 to 0), the number of levels within the scale (e.g. 4, 6 or 8), the type of scale (e.g. linear, logarithmic) and the boundaries between the levels according to the situation.

The index may be a subject-based index in which state of each subject is compared to the reference state of the subject itself. The subject-based index gives information about whether the subject state of consciousness has been modified by the treatment session.

The index may be a population-based index in which the state of each subject is compared to population-based reference state. The population-based index allows the state of the subject to be compared to the overall population. It can allow an objective indication of whether, for instance, a subject can undergo an intervention (e.g. invasive surgery) safely while under non-pharmacological sedation.

With respect to the subject-based index, a reference state e.g. a reference value for one or more of DoD, DoH, DoS is measured for the subject before the treatment session.

During the treatment session, based on response data, realtime values for one or more of DoD, DoH, DoS is measured for the subject. During the treatment session, based on a comparison between the reference value and the realtime DoD, DoH, DoS values, realtime values for one or more of DoDI, DoHI, DoSI is calculated. The subject-based index and exemplary calculations for each of DoDI, DoHI, DoSI is described in more detail below.

With respect to the population-based index, a reference state e.g. a reference value for one or more of DoD, DoH, DoS is drawn from a database. The database reference values are based on population studies. The reference value may vary according to certain factors include age, gender, ethnicity, intervention characteristics hence, the reference value may be adapted according to the subject and/or the user. During the treatment session, based on response data, realtime values for one or more of DoD, DoH, DoS is measured for the subject. During the treatment session, based on a comparison between the database reference value and the realtime DoD, DoH, DoS values, real time values for one or more of DoDI, DoHI, DoSI is calculated. The population-based index and exemplary calculations for each of DoDI, DoHI, DoSI is described in more detail below.

Provided herein is a method for determining and/or monitoring a level of non-pharmacologically-optionally with pharmacologically-modified state (i.e. mixed) of consciousness of a subject receiving a treatment session, the method comprising the steps of:
  receiving response data representing a subject's response to the treatment session;
  transforming the response data into a depth of state (DoS) index (DoSI) and/or a depth of hypnosis (DoH) index (DoHI), the DoHI and/or DoSI representing a measure of the non-pharmacologically optionally with mixed (non-pharmacologically- and pharmacologically)—modified state of consciousness of the subject.

Provided herein is a method for determining and/or monitoring a level of non-pharmacologically-optionally with pharmacologically-modified state (i.e. mixed) of consciousness of a subject receiving a treatment session, the method comprising the steps of:
  receiving response data representing a subject's response to the treatment session;
  determining from the response data a Depth of Dissociation (DoD) Index (DoDI);
  determining from the DoDI, a depth of state (DoS) index (DoSI) and/or a depth of hypnosis (DoH) index (DoHI), the DoHI representing a measure of the non-pharmacologically-modified state of consciousness of the subject and the DoSI representing a measure of the non-pharmacologically optionally with mixed (non-pharmacologically—and pharmacologically)—modified state of consciousness of the subject.

Preferably the DoSI and/or DoHI is determined from the DoDI. Preferably the DoHI is determined from the DoDI.

The method may give an indication of a current DoSI and/or DoHI of the subject.

The method may give an indication of a current DoSI and/or DoHI of the subject, and an expected DoSI and/or DoHI at that point in time of the treatment session. The expected DoSI and/or DoHI at that point in time may be determined from a population-based expectation.

The method may give an indication of a trend of the DoSI and/or DoHI of the subject during the treatment session. The trend of DoSI and/or may be determined from a population-based expectation.

The method may determine and/or monitor a level of non-pharmacologically-modified state of consciousness. The method may determine and/or monitor a level of combined or mixed non-pharmacologically-modified and pharmacologically-modified state of consciousness. The method may determine and/or monitor:
  a level of non-pharmacologically-modified state of consciousness;
  and optionally a level of mixed (combined) non-pharmacologically-modified and pharmacologically-modified state of consciousness.

The DoSI may be the sum of the different depths of state indexes. The DoSI may be the sum of DoHI and other contributions to the state such as by a pharmacological treatment.

The DoSI may be equal to DoHI, particularly when treatment session contains only hypnosis.

A ratio of DoSI and DoHI (a derived index) may have a scale with a first and second limit.

The first limit may represent no modified state of consciousness and the second limit may represent the deepest modified state of consciousness. The first limit may represent an initial (reference) state of the subject. The first limit may represent no/lightly modified state of consciousness and the second limit may represent a fully/deeply modified state of consciousness. The first limit may represent a light trance, and the second limit may represent a deep trance. The first and second limits may be numerically represented e.g. 0 to 100, 100 to 0, 0 to 1, 1 to 0 respectively. The second limit may be higher than the first limit, or the first limit may be higher than the second limit. The choice of a higher number for the second limit may depend on the subject or user perspective. A subject with a DoSI and DoHI ratio towards the second limit, for instance, can receive a surgical intervention when the modified state of consciousness is for anaesthetic effect. An anaesthetist may have a preference that the first limit is higher (e.g. 1, 100, 100%) than the second limit (e.g. 0, 0%).

It is appreciated that the terms DoH, DoHI, DoS, DoSI may be accorded other names in a practical implementation of the invention, for instance, due to regional sensitives or language translations.

DoSI and/or DoHI may be indicative of a number of different levels of consciousness and/or dissociation of the subject. The number of levels may be any, for instance 3 to 10, preferably 4 to 8 levels. There may be 4, 6, or 8 levels. The levels may divided be within the first and second limits. The division may be even (linear), logarithmic, or according to another scheme. The lowest level (e.g. $1^{st}$ level) may correlate with or contain the first limit, the highest level (e.g. $4^{th}$ level) may correlate with or contain the second limit. When a DoSI and/or DoHI is a value between 100 (first limit) and 0 (second limit) and the number of levels is 4, the 4 levels may be 100-76 ($1^{st}$ level), 75 to 51 ($2^{nd}$ level), 50 to 26 ($3^{rd}$ level), 25 to 0 ($4^{th}$ level). It is appreciated that the end points of the levels may allow a continuous numerical scale (not interrupted) into the next level. When the DoSI and/or DoHI is a value between 100 (first limit) and 0 (second limit) and the number of levels is 8, the 8 levels may be 100-87.5 ($1^{st}$ level), 87.5 to 75 ($2^{nd}$ level), 75 to 62.5 ($3^{rd}$ level), 62.5 to 50 ($4^{th}$ level), 50 to 37.5 ($5^{th}$ level), 37.5 to 25 ($6^{th}$ level), 25 to 12.5 ($7^{th}$ level), 12.5 to 0 ($8^{th}$ level). The skilled person would be able to determine the extent of the scale (e.g. 100 to 0, or 60 to 0), the number of levels within the scale (e.g. 4, 6 or 8), the type of scale (e.g. linear, logarithmic) and the boundaries between the levels according to the situation.

DoSI and/or DoHI may be indicative of at least 3 of the following levels of the subject during the treatment session:
  (a) a first level, subject is conscious, alert, agitated if provoked;
  (b) a second level, subject is conscious and calm, but not dissociated;
  (c) a third level, subject is in a light dissociated state;
  (d) a fourth level, the subject is deep in the dissociated state/immersive state.

Alternatively, DoSI and/or DoHI may be indicative of at least three of the following levels during the treatment session:
  (i) a first level, characterised by the subject being awake and alert with minimal to no cognitive impairment;
  (ii) a second level, characterised by the subject being awake but tranquil, capable of purposeful response to verbal commands at conversational level;
  (iii) a third level, characterised by the subject appearing asleep but still capable of purposeful response to verbal commands at conversational level;
  (iv) a fourth level, characterised by the subject appearing asleep but still capable of purposeful response to louder verbal commands or glabellar tap;
  (v) a fifth level, characterised by the subject being or appearing to be asleep, but still capable of sluggish purposeful responses to glabellar tap or loud verbal commands;
  (vi) a sixth level, characterised by the subject being or appearing to be asleep with sluggish response to external stimuli;
  (vii) a seventh level, characterised by the subject being asleep with reflexive responses to nociceptive stimulus
  (viii) an eight level, characterised by the subject being unresponsive to external stimuli, including firm pressure or nociceptive stimulus.

Described herein is a method for determining a depth of state (DoS) index (DoSI), the DoSI representing a measure of a non-pharmacologically-optionally (mixed) with a pharmacologically-modified state of consciousness of the subject, comprising the determining a state of consciousness according to a method described herein. Preferably the DoSI is determined from at least the DoD/H. Preferably wherein the DoSI is determined from at least the DoD/H.

Described herein is a method for determining a depth of hypnosis (DoH) index (DoHI), the DoHI representing a measure of a non-pharmacologically-modified state of consciousness of the subject, comprising the determining a state of consciousness according to a method described herein. Preferably the DoHI is determined from at least the DoD.

The response data may be transformed into an index e.g. into a DoDI, DoHI, DoSI using an evaluation protocol. The evaluation protocol may comprise use of one or more of a mathematical (e.g. statistical) model, trained machine-leaning model, mathematical index, reference data. The evaluation protocol takes as input the response data and/or independently measured data of one or more of DoDI, DoHI, DoSI, and outputs the index.

The evaluation protocol may include a step of extracting from the response data one or more of the Group 1 indicator, Group 2 indicator.

The measured data may comprise one or more data components. A data component is attributed to a single measurement (e.g. EEG, EMG, EDA, or ECG), single observation (e.g. movement, skin colour), or single self-reported event (e.g. level of dissociation).

The evaluation protocol may weight the data components of the response data equally or differently. The weighting given to a data component depends, amongst other things, on relevance and precision of the component. For instance, the evaluation protocol may give EEG data may have a higher rating, reflecting its high relevance and precision. The evaluation protocol may use data components which have less relevance and precision, that are still indicative enough for the situation. In some situations, the response data may comprise a smaller number of data components that have high relevance and precision that are indicative enough for the situation. In some situations, the response data may comprise a larger number of data components that have lower relevance and precision that are indicative enough for the situation.

The evaluation protocol may be refined as more subjects are evaluated using the method. A method of refining the evaluation protocol may comprise:
  receiving response data representing a subject's response to the treatment session,
  receiving independently measured data of one or more of DoDI, DoHI, DoSI,
  using the response data and independently measured data to refine the evaluation protocol.

A method of refining the evaluation protocol may comprise:
  Receiving measured response data representing a subject's response to the treatment session,
  Receiving self-reported and/or observational measure of DoS and/or DoH and/or DoD;
  Receiving independently measured data of DoS and/or DoH and/or DoD;
  Using the response data, the self-reported and/or observational data, and the independently measured data to refine the evaluation protocol The evaluation protocol may additionally or alternatively be refined using analytics. The data collected during previous treatment session may contribute a refinement of the evaluation protocol.

As the evaluation protocol is created and/or refined, it may be apparent that one or more data components of the response data become redundant in determining and/or monitoring the level of non-pharmacologically-optionally with pharmacologically-modified (mixed) state of consciousness of a subject. It is an aspect of the invention that at least one, preferably all of measured data, observation data and response data are used to create and/or refine the evaluation protocol. It is an aspect of the invention that only measured data is used in the method.

An example of an evaluation protocol for determining a DoDI is set out below. Generally speaking, it may comprise 5 principal steps:
  Step 1: receive and digitise response data during a treatment session from F-EEG-electrode and optionally P-EEG electrode.
  Step 2: generate:
    Group 1 indicators i.e. F-power (dt), and optionally P-power (dt) from the digitised response data and/or Group 2 indicators i.e. F-MSPA.
  Step 3: generate one or more indicator value from step 2), using for instance, integrative analysis
  Step 4: comparing the value of Step 3) with reference values (population-based index or subject-based index)
  Step 5: obtain from Step 4) a DoDI index e.g. a number of a scale 0 to 20, or a word, or category.

In step 2, the digitised response data may undergo a pre-processing protocol including one or more of re-referencing to average reference, bandpass and/or notch filtering to exclude low and high frequency artifacts, signal segmentation into so called epochs, artifact rejection (ocular, muscular, . . . ), and baseline adjustment. Segmentation in to epochs refers to a procedure in which specific time-windows are extracted from the continuous EEG signal.

These time windows are called "epochs", and usually are time-locked with respect an event, e.g. electrical stimulus. ERP or MSPA are measured based on epochs. For time domain analysis of EEG signals, there is typically peak detection to determine peak amplitude and latency (in form of a time series if multiple epochs), and mathematical transformations performed (e.g.: mean or change variable if multiple epochs). For a frequency domain analysis of EEG signals: there is typically a time to frequency transform (e.g. Fourier transform), relevant frequency bands (e.g. delta-theta (td)) are extracted, amplitude/power and phase for each frequency band (and each epoch) are determined, and mathematical transformations performed (e.g: mean if multiple epochs). From this, one obtain at least one of the following features for at least one electrode: delta-theta (td) frequency band related amplitude/power, delta-theta (td) frequency band related phase, EEG mean signal peak-to-peak amplitude (MSPA), EEG MSPA latency. There may be a normalization step for instance to correct for the time of intervention to ensure that every subject contributes similarly.

In step 3, one or more indicator values are generated using integrative analysis, for instance, using the equation:

$$DoD_{s,t} = \sum_{i=1}^{n} (\alpha_i f_i(F_{i,s,[t',t]}))$$

Where $\alpha_i$ is an optional parameter that evolves with the population size and characteristics, and may be determined using learning processes based on response data and/or independently measured data of the DoD, $f_i$ is a function determined using learning processes based on response data and/or independently measured data of the DoD, $F_{i,s,[t',t]}$ is the value(s) of the feature obtained from point 2 from time t' to time t (t'<t) and for the subjects. The upper [t'–t] interval means that the value of dissociation at time t may be computed based on features extracted from several $F_{i,s}$ values. As example, taking the mean and the standard deviation from the past x milli-seconds leave to a more sensitive and more robust determination of DoDI.

In step 4, there is a comparison of values with reference values
If the index is a subject-based index (each subject is its own control).

$$\Delta_a DoD_{s,t} = S(\beta(DoD_p^* - DoD_{s,[t',t]}) + K)$$

If the index is population-based (absolute) and that subject s is part of population p, $$\Delta_r DoD_{s,t} = S(\beta(DoD_{s,p}^* - DoD_{s,[t',t]}) + K)$$

Where S is a scale-up parameter, β is a parameter accounting for the population characteristics (age, sex, ethnicity, . . . ) determined using learning processes based on response data and/or independently measured data of the DoD, $DoD^*_{s,p}$ is the individual/subject-based reference state, $DoD^*_p$ is the absolute/population-based reference state determined using learning processes based on response data and/or independently measured data of the DoD, and K is a "translation" parameter allowing to adjust thresholds based on user preference.

In step 5 the DoDI index is generated. The value obtained in step 4 is compared with a predefined scale depending on subject/intervention characteristics determined following process described in the refine protocol below (Using trained machine-learning models and/or artificial intelligence, based on collected measured, observed and self-reported data/reference data).

In DoDI, the index may be a population-based index_ (absolute scale, a subject is compared with a population). The first limit may represent "no dissociation", or full attention regarding stimulus coming from the actual environment and/or regarding internal event. The second limit may represent "the most complete dissociation", or complete inattention regarding stimulus coming from the actual environment and/or regarding internal event; the subject has fully a feeling of being present in an alternative reality.

Intermediate values represent intermediate levels of dissociation which are intermediate levels of inattention regarding stimulus coming from the actual environment and/or regarding internal event.

In DoDI, the index may be a subject-based index (relative scale, each subject compared with itself). The first limit may indicate that the subject is dissociated as initially (reference state). The subject's degree of inattention regarding stimulus coming from the actual environment and/or regarding internal event is the same as before the treatment session. The second limit may indicate that the subject is fully dissociated. The subject's degree of inattention regarding stimulus coming from the actual environment and/or regarding internal event is maximal (for itself); the subject has fully a feeling of being present in an alternative reality. Intermediate values represent intermediate levels of dissociation which are intermediate levels of inattention regarding stimulus coming from the actual environment and/or regarding internal event.

An example of an evaluation protocol for determining a DoHI is set out below. In this protocol, steps 1 and 2 generate one or more groups indicators 1 to 2 from the response data. Generally speaking, it may comprise 5 principal steps:

Step 1: receive and digitise response data during a treatment session from F-EEG-electrode and optionally P-EEG electrode;
Step 2: generate one or more of Group indicators 1 to 2;
Step 3: generate one or more indicator values from step 2), using for instance, integrative analysis;
Step 4: comparing the value of Step 3) with reference values (population-based index or subject-based index);
Step 5: obtain from Step 4) a DoHI index e.g. a number of a scale 0 to 20, or a word, or category.

Alternatively, the evaluation protocol for determining a DoHI may be based on one or more of DoDI already generated. Steps 1 and 2 may be replaced with steps of obtaining one or more of DoDI, and normalising them.

Step 1: Obtain DoDI;
Step 2: Normalise one or more of DoDI;
Step 3: generate one or more indicator values from step 2), using for instance, integrative analysis;
Step 4: comparing the value of Step 3) with reference values (population-based index or subject-based index);
Step 5: obtain from Step 4) a DoHI index e.g. a number of a scale 0 to 20, or a word, or category.

In step 2, the normalise step is a transformation to bring one or more of DoDI to a comparable scale.

In step 3, one or more indicator values is generated using integrative analysis, for instance, using the equation:

$$DoH_{s,t} = \sum_{i=1}^{n} (\alpha_i f_i(F_{i,s,[t',t]}))$$

Where $\alpha_i$ is an optional parameter that evolves with the population size and characteristics, and may be determined using learning processes based on response data and/or computed DoD, DoH and/or independently measured data of the DoD, DoH, $f_i$ is a function determined using learning processes based on response data and/or computed DoD, DoH and/or independently measured data of the DoD, DoH, $F_{i,s,[t',t]}$ is the value(s) of the feature obtained from point 2 from time t' to time t (t'<t) and for the subjects.

In step 4, there is a comparison of values with reference values.

If the index is a subject-based index (each subject is its own control), $$\Delta_r DoH_{s,t} = S(\beta(DoH^*_{s,p} - DoH_{s,t}) + K)$$

If the index is population-based (absolute) and that subject s is part of population p, $$\Delta_a DoH_{s,t} = S(\beta(DoH^*_p - DoH_{s,t}) + K)$$

Where S is a scale-up parameter, β is a parameter accounting for the population characteristics (age, sex, ethnicity, . . . ) determined using learning processes based on response data and/or computed DoD, DoH and/or independently measured data of the DoD, DoH, and $DoH^*_{s,p}$ is the individual/subject-based reference state, $DoH^*_p$ is the absolute/population-based reference state determined using learning processes based on response data and/or computed DoD, DoH and/or independently measured data of the DoD, DoH, and K is a "translation" parameter allowing to adjust thresholds based on user preference.

In step 5 the DoHI index is generated. The value obtained in step 4 is compared with a predefined scale depending on subject/intervention characteristics determined following process described below in the section "refinement of the evaluation protocol", (Using trained machine-learning models and/or artificial intelligence, based on collected measured, observed and self-reported data/reference data).

In DoHI, the index may be a population-based index_ (absolute scale, a subject is compared with a population). The first limit may indicate that the subject level of consciousness is similar to the level of consciousness generally observed for normal awake subjects. The second limit may represent the deepest modified state of consciousness, or completely reduced perception of peripheral stimuli and a subject's modified perception of the self and the self in the environment. Intermediate values represent intermediate levels of modified state of consciousness.

In DoHI, the index may be a subject-based index (relative scale, each subject compared with itself). The first limit may indicate that the subject state of consciousness is not (or not significantly) modified as compared to the reference state; Both the subject perception of peripheral stimuli and perception of the self and the self in the environment are not modified as compared to the reference state. The second limit may indicate that the subject state of consciousness is fully/deeply modified as compared to the reference state.

Intermediate values represent intermediate levels of modified state of consciousness. An example of an evaluation protocol for determining a DoSI is set out below. In this protocol, steps 1 and 2 generate one or more groups indicators 1 to 2 from the response data. Generally speaking, it may comprise 5 principal steps:

Step 1: receive and digitise response data during a treatment session from F-EEG-electrode and optionally P-EEG electrode.
Step 2: generate one or more of Group indicators 1 to 2
Step 3: generate one or more indicator values from step 2), using for instance, integrative analysis
Step 4: comparing the value of Step 3) with reference values (population-based index or subject-based index)
Step 5: obtain from Step 4) a DoSI index e.g. a number of a scale 0 to 20, or a word, or category.

Alternatively, the evaluation protocol for determining a DoSI may be based on one or more of DoDI already generated. Steps 1 and 2 may be replaced with steps of obtaining one or more of DoDI, and normalising them.

Step 1: Obtain DoDI.
Step 2: Normalise one or more of DoDI.
Step 3: generate one or more indicator values from step 2), using for instance, integrative analysis
Step 4: comparing the value of Step 4) with reference values (population-based index or subject-based index)
Step 5: obtain from Step 3) a DoSI index e.g. a number of a scale 0 to 20, or a word, or category.

Alternatively, the evaluation protocol for determining a DoSI may be based on one or more of DoDI already generated. Steps 1 and 2 may be replaced with steps of obtaining one or more of DoDI, and normalising them.

Step 1: Obtain one or more of DoDI, a measure of state consciousness induced pharmacologically, a measure of state of consciousness induced by other treatments;
Step 2: Normalise one or more of DoDI, measure of state of consciousness induced pharmacologically, measure of state of consciousness induced by other treatments;
Step 3: generate one or more indicator values from step 2), using for instance, integrative analysis
Step 4: comparing the value of Step 4) with reference values (population-based index or subject-based index)
Step 5: obtain from Step 3) a DoSI index e.g. a number of a scale 0 to 20, or a word, or category.

In step 2, the normalise step is a transformation to bring one or more of DoDI, measure of state of consciousness induced pharmacologically, measure of state of consciousness induced by other treatments to a comparable scale.

In step 3, one or more indicator values is generated using integrative analysis, for instance, using the equation:

$$DoS_{s,t} = \sum_{i=1}^{n} (\alpha_i f_i(F_{i,s,[t',t]}))$$

Where $\alpha_i$ is an optional parameter that evolves with the population size and characteristics, using learning processes based on response data and/or computed one or more of DoD, DoH, DoS, measure of state of consciousness induced pharmacologically, measure of state of consciousness induced by other treatments and/or independently measured data of the one or more of DoD, DoH, DoS, measure of state of consciousness induced pharmacologically, measure of state of consciousness induced by other treatments, $f_i$ is a function determined using learning processes based on response data and/or computed one or more of DoD, DoH, DoS, measure of state of consciousness induced pharmacologically, measure of state of consciousness induced by other treatments and/or independently measured data of the one or more of DoD, DoH, measure of state of consciousness induced pharmacologically, measure of state of consciousness induced by other treatments, $F_{i,s[t',t]}$ is the value(s) of the feature obtained from point 2 from time t' to time t (t'<t) and for the subjects.

In step 4, there is a comparison of values with reference values If the index is a subject-based index (each subject is its own control), $$\Delta_r DoS_{s,t} = S(\beta(DoS^*_{s,p} - DoS_{s,t}) + K)$$

If the index is population-based (absolute) and that subject s is part of population p, $$\Delta_G DoS_{s,t} = S(\beta(DoS^*_p - DoS_{s,t}) + K)$$

Where S is a scale-up parameter, $\beta$ is a parameter accounting for the population characteristics (age, sex, ethnicity, . . . ) using learning processes based on response data and/or computed DoD, DoH, DoS, measure of state of consciousness induced pharmacologically, measure of state of consciousness induced by other treatments and/or independently measured data of the DoD, DoH, measure of state of consciousness induced pharmacologically, measure of state of consciousness induced by other treatments, $DoS^*_{s,p}$ is the individua/subject-based reference state, $DoS^*_p$ is the absolute/population-based reference state determined using learning processes based on response data and/or computed DoD, DoH, DoS and/or independently measured data of the DoD, DoH, Do, and K is a "translation" parameter allowing to adjust thresholds based on user preference.

In step 5 the DoSI index is generated. The value obtained in step 4 is compared with a predefined scale depending on subject/intervention characteristics determined following process described below in the section "refinement of the evaluation protocol", (Using trained machine-learning models and/or artificial intelligence, based on collected measured, observed and self-reported data/reference data).

In DoSI, the index may be a population-based index_ (absolute scale, a subject is compared with a population). The first limit may represent "no modified state of consciousness". The first limit may indicate that the subject level of consciousness is similar to the level of consciousness generally observed for normal awake subjects. The second limit may represent the deepest modified state of consciousness, or completely reduced perception of peripheral stimuli and a subject's modified perception of the self and the self in the environment. Intermediate values represent intermediate levels of modified state of consciousness.

As mentioned elsewhere, DoSI can be a measure of DoHI optionally with measure of state of consciousness induced pharmacologically and optionally with a measure of state of consciousness induced by other treatments.

In DoSI, the index may be a subject-based index (relative scale, each subject compared with itself). The first limit may indicate that the subject state of consciousness is not (or not significantly) modified as compared to the reference state; Both the subject perception of peripheral stimuli and perception of the self and the self in the environment are not modified as compared to the reference state. The second limit may indicate that the subject state of consciousness is fully/deeply modified as compared to the reference state. Intermediate values represent intermediate levels of modified state of consciousness. As mentioned elsewhere, DoSI can be a measure of DoHI optionally with measure of state of consciousness induced pharmacologically and optionally with a measure of state of consciousness induced by other treatments.

When more subjects have been evaluated, more data becomes available which can be used to refine the evaluations protocols for each of DoDI, DoHI and DoSI. Described herein are exemplary ways (a) to (c) in which the respective evaluation protocols can be refined, using at least one, preferably all of measured data, observational data and self-reported data.

(a) Model parameter's incrementation

Model parameters ($\alpha_i, f_i, \beta$) are evaluated based on measured data, and self-reported or independently measured DoD(I), DoH(I) and/or DoSI, using mathematical and/or statistical and/or machine learning processes.

As the evaluation protocol is refined, it may be apparent that one or more data components of the response data become redundant in determining and/or monitoring the level of consciousness/dissociation of a subject. This data will automatically be weighted by a (close to) zero weights $\alpha_i$ when using the upper described method.

(b) Identifying new relevant features for the computation of DoS/DoD/DoH and including them in the evaluation protocol With new incoming data, it may be apparent that one or more data components of the response data appears as relevant in determining and/or monitoring the level of consciousness/dissociation of a subject and should be included it in the evaluation protocol. New model's parameters should be modified accordingly as described above.

(c) Building population-based reference states/thresholds

Population-based thresholds and/or reference state are computed based on measured data and/or observed data and/or self-reported and/or computed DoD(I), DoH(I), DoS (I) and/or independently measured DoD(I), DoH(I) and DoSI, using mathematical and/or statistical and/or machine learning processes. They should further be validated for convergence and stability.

The response data is transformed into the DoSI and/or DoHI using an evaluation protocol. The evaluation protocol may comprise use of one or more of a mathematical (e.g. statistical) model, trained machine-leaning model, mathematical index, reference data. The evaluation protocol takes as input the response data, and outputs the DoSI and/or DoHI.

The measured data may comprise one or more data components. A data component is attributed to a single measurement (e.g. EEG, EMG, EDA, or ECG), single observation (e.g. movement, skin colour), or single self-reported event. The evaluation protocol may weight the data components of the response data equally or differently. The weighting given to a data component depends, amongst other things, on relevance and precision of the component. For instance, the evaluation protocol may give EEG data may have a higher rating, reflecting its high relevance and precision. The evaluation protocol may use data components which have less relevance and precision, that are still indicative enough for the situation. In some situations, the response data may comprise a smaller number of data components that have high relevance and precision that are indicative enough for the situation. In some situations, the response data may comprise a larger number of data components that have lower relevance and precision that are indicative enough for the situation.

The evaluation protocol may be refined as more subjects are evaluated using the method.

A method of refining the evaluation protocol may comprise
- receiving response data representing a subject's response to the treatment session,
- receiving independently measured data of the DoSI and/or DoHI,
- using the response data and independently measured data to refine the evaluation protocol.

The evaluation protocol may additionally or alternatively be refined using analytics. The data collected during previous treatment session may contribute a refinement of the evaluation protocol.

As the evaluation protocol is created and/or refined, it may be apparent that one or more data components of the response data become redundant in determining and/or monitoring the level of non-pharmacologically-optionally with pharmacologically-modified (mixed) state of consciousness of a subject. It is an aspect of the invention that at least one, preferably all of measured data, observation data and response data are used to create and/or refine the evaluation protocol. It is an aspect of the invention that only measured data is used in the method.

The method and system may determine an expected DoSI and/or DoHI and DoHI ratio for a point in time of the treatment session, based on position (and acts of treatment already performed) in the treatment session. For instance, if the treatment comprises a hypnotic session, an expected DoSI and/or DoHI may be determined from the phase (i.e. one of (i) to (iv) described above) of the hypnotic session and from the position within the phase.

For instance, if the treatment comprises a pharmacological sedation session, an expected DoSI may be determined from the dose of sedative. The expected DoSI and/or DoHI may be determined from population data, namely from historical or precedence data Because the administered treatment does not always lead to the expected depth of state, a difference between the measured depth of state and expected depth of state gives the user guidance for corrective measures.

The method and system may provide an output to a graphical user interface (GUI). The system may comprise a GUI.

The output to the GUI may be graphical and/or numerical. The output to the GUI may indicate one or more of:
- current level or modified state of consciousness;
- current DoSI and/or DoHI;
- current DoS and/or DoH;
- current DoDI;
- current DoD;
- current ratio between DoSI and DoHI (a derived index);
- current ratio between two of DoSI, DoHI, DoDI.
- trending state of consciousness;

trending (historical) DoSI and/or DoHI;
trending (historical) DoSI and/or DoHI and/or DoDI;
trending (historical) DoS and/or DoH;
trending (historical) DoS and/or DoH and/or DoD;
trending (historical) ratio between two of DoSI, DoHI;
trending (historical) ratio between two of DoSI, DoHI, DoDI;
expected state of consciousness;
expected DoSI and/or DoHI;
expected DoSI and/or DoHI and/or DoDI;
expected DoS and/or DoH;
expected DoS and/or DoH and/or DoD;
expected ratio between DoSI and DoHI;
expected ratio between two of DoSI, DoHI, DoDI.

The output to the GUI may additionally or alternatively show one or more current data components (e.g. one or more measured data components, one or more observed data components, and/or one or more self-reported data components). Examples of current data components include those listed elsewhere herein, preferably one or more of EEG data, EMG data, and pulse rate data.

The output to the GUI may comprise a graphical indicator wherein a position and/or colour on the screen provide the user (e.g. doctor) an indication of the state of the subject and if necessary steps to be taken. For example, a green colour may indicate a positive status in terms of patient experience of signal for the user. For example, a red colour may indicate a negative status in terms of patient experience of signal for the user. For example, a left position may indicate a positive status in terms of patient experience of signal for the user. For example, a right position may indicate a negative status in terms of patient experience of signal for the user. For example, an upper position may indicate a positive status in terms of patient experience of signal for the user. For example, a lower position may indicate a negative status in terms of patient experience of signal for the user. The output to the GUI may additionally or alternatively show one or more derived indexes. A derived index is an index derived from one or more data components and/or from DoSI and/or from DoHI. For instance, a comfort index might be a derived index based on skin conductance data and EEG data. A postoperative amnesia index might be a derived index based on a combination of EEG and EMG data. Another derived index might be based on a ratio of DoHI and DoSI. These derived indexes may be based on collected data as observed for the subject, optionally refined using analytics (i.e. historical/population data). A graphical output may comprise a timeline and a marker on the timeline indicating the DoSI and/or DoHI and/or ratio thereof. The DoSI and/or DoHI and/or ratio thereof may be on scale with a first and second limit e.g. 0 to 1, 0 to 100.

The GUI may show the current DoSI on one or more scales between the first and second limits; the scale may be linear, logarithmic, or other. The scale may be continuous, categorical, discreet, percentage, ratio.

Examples of GUIs (200, a to g) are given in FIGS. 2 to 9.

Figure 2:
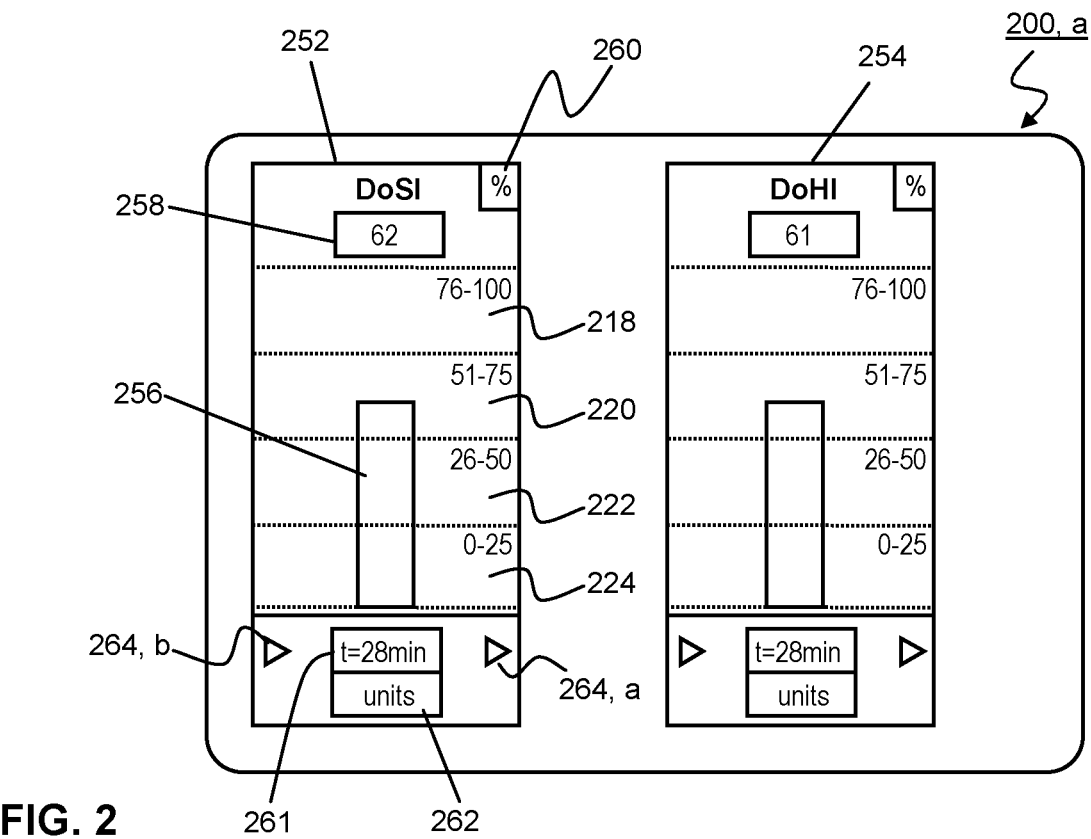
FIGS. 2 to 9 illustrate examples of outputs to a graphical user interface.

FIG. 2 shows a GUI (200, a) that is a graphical display of current status of DoSI and DoHI as separate bar charts (252, 254 respectively). Reference is made to the DoSI bar chart (252); the DoHI bar chart contains equivalent features (not labelled). The DoSI (y-axis) bar chart displayed is divided into 4 zones: 0-25% (224), 26-50% (222), 51-75% (220), 76-100% (218); these may optionally be coloured to indicate a level of safety (e.g. 76-100%-red, 51-75%—orange, 26-50%—light green, 0-25%—deep green. The 100-76% (218, red) zone may indicate that the subject is conscious, alert, agitated if provoked: wait for hypnotic session to advance and optionally administer analgesic. The 75-50% (220, orange) zone may indicate that the subject is conscious and calm, but not dissociated, not yet ready. The 50-26% (222, light green) zone may indicate that the subject is in a light dissociated state, not yet ready. The 0-25% (224, deep green) zone may indicate that the subject is deep in the dissociated state/immersive state. It is appreciated that the units of percent and the extent of the scale of 0 to 100% is exemplary, and other units (e.g. unitless) and scales (e.g. 0 to 1, 0 to 40, 0 to 50, 0 to 60 etc, linear, logarithmic) are within the scope of the disclosure. The height of the bar (256) is indicative of the DoSI at the indicated time (261). A numerical display (258) also indicates the DoSI. Current units (percent) are indicated (260), that can be changed (e.g. to unitless and/or other units) with a units button (262). Forwards (264, a) and backwards (264, b) buttons allow the display to scroll back and forth between current DoSI and previous readings. It is appreciated that DoHI may be be replaced with DoDI, and the information described above applied also to this index, either separate from or combined with DoSI.

Figure 3A:
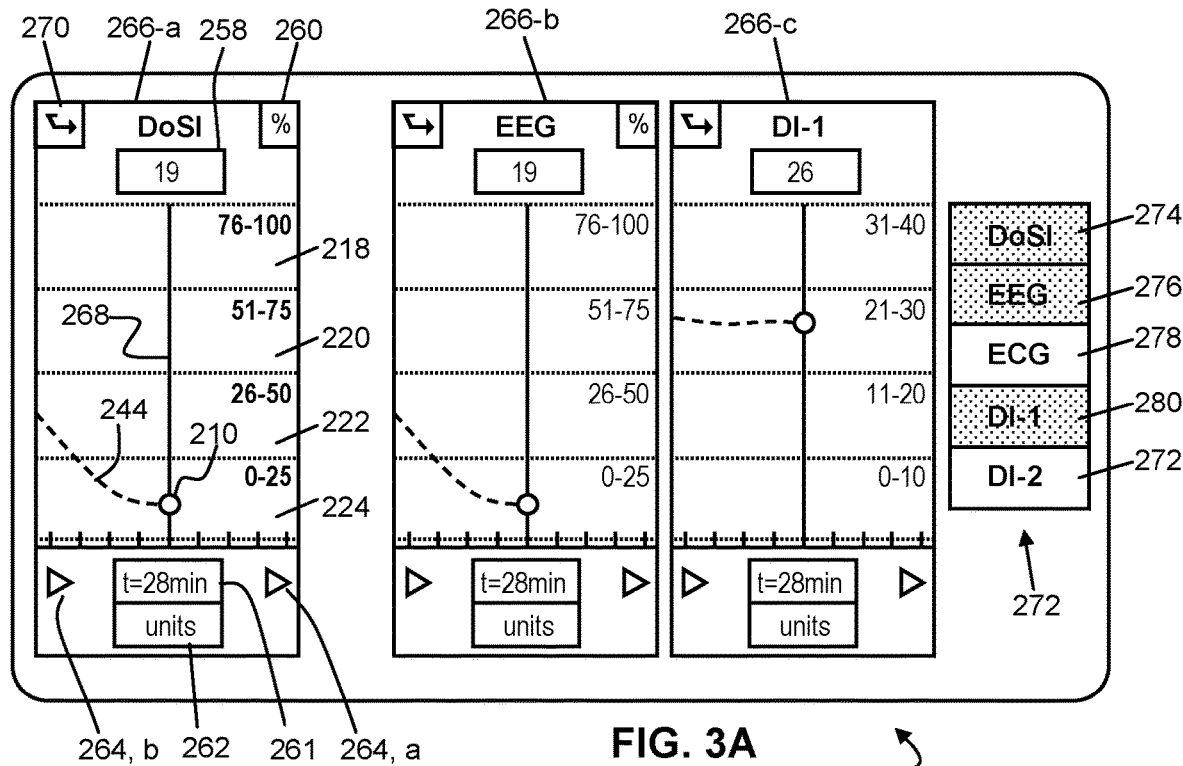
Figure 3B:
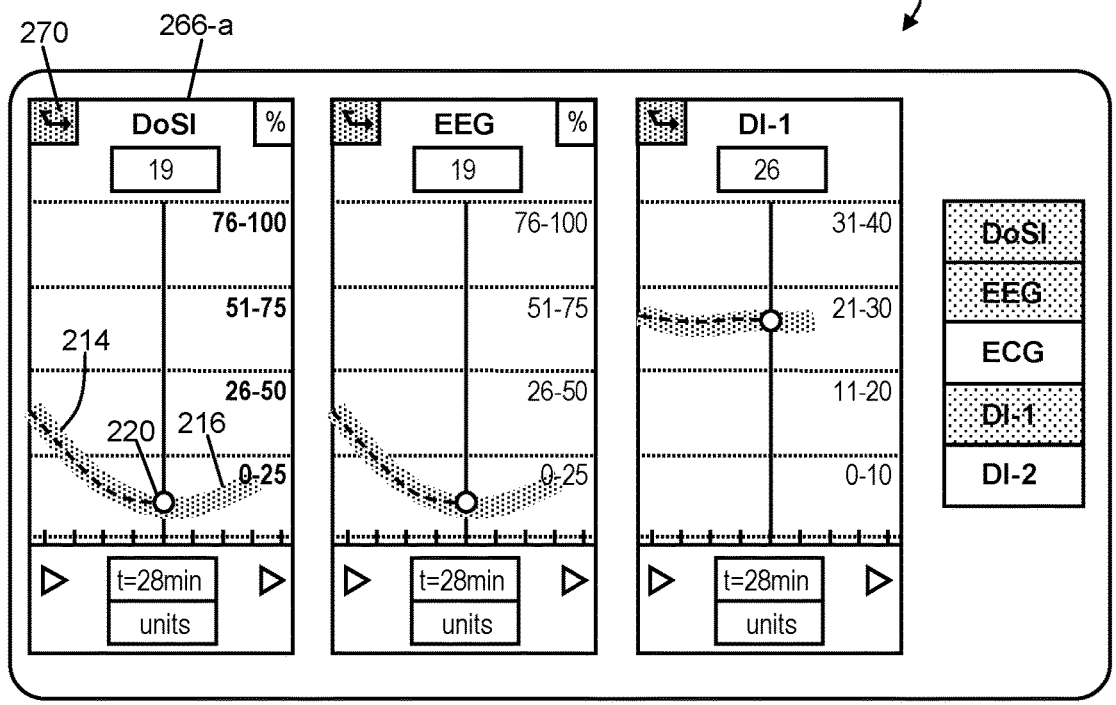

FIGS. 3A and 3B shows a GUI (200, b) that is graphical display of current status of DoSI, EEG and derived index-1 (DI-1) as separate scroll charts (266-a 266-b, 266-c respectively). Reference is made to the DoSI scroll chart (266-a) in FIG. 3A; the other scroll charts contain equivalent features (not labelled). The DoSI scroll chart displayed is divided into 4 zones: 0-25% (224), 26-50% (222), 51-75% (220), 76-100% (218); these may optionally be coloured to indicate a level of safety (e.g. 76-100%—red, 51-75%-orange, 26-50%—light green, 0-25%—deep green as in FIG. 2. The DoSI scroll chart (266-a) contains a stationary time axis (268) along which the DoSI reading (210) at the indicated time (261) slides (up and down). A numerical display (258) also indicates the DoSI. The time axis (268) remains static, while the background scrolls in the direction of the time (typically from right to left). Historical or trending datapoints (244) are indicated.

Current units (percent) are indicated (260) that can be changed (e.g. to unitless and/or other units) with a 'units' button (262). Forwards (264, a) and backwards (264, b) buttons allow the display to scroll back and forth between current DoSI and previous readings. A panel of buttons (272) allows the user to choose from a selection of scroll charts for display: buttons for DoSI (274), EEG (276) and DI-1 (280) are selected (grey background), and the selected scroll charts are displayed (266-a, 266-b, 266-c respectively). Unselected are buttons for ECG (278) and DI-2 (derived index-2, 272)).

In FIG. 3B, the same GUI as FIG. 3A are shown, and button (270) is unselected in FIG. 3A and is selected in FIG. 3B; button (270) toggles on or off a display of expected DoSI (216) for the subject that is superimposed on the scroll chart; current DoSI (210) and historical DoSI (214) can be visually compared with the expected DoSI (216).

Figure 4A:
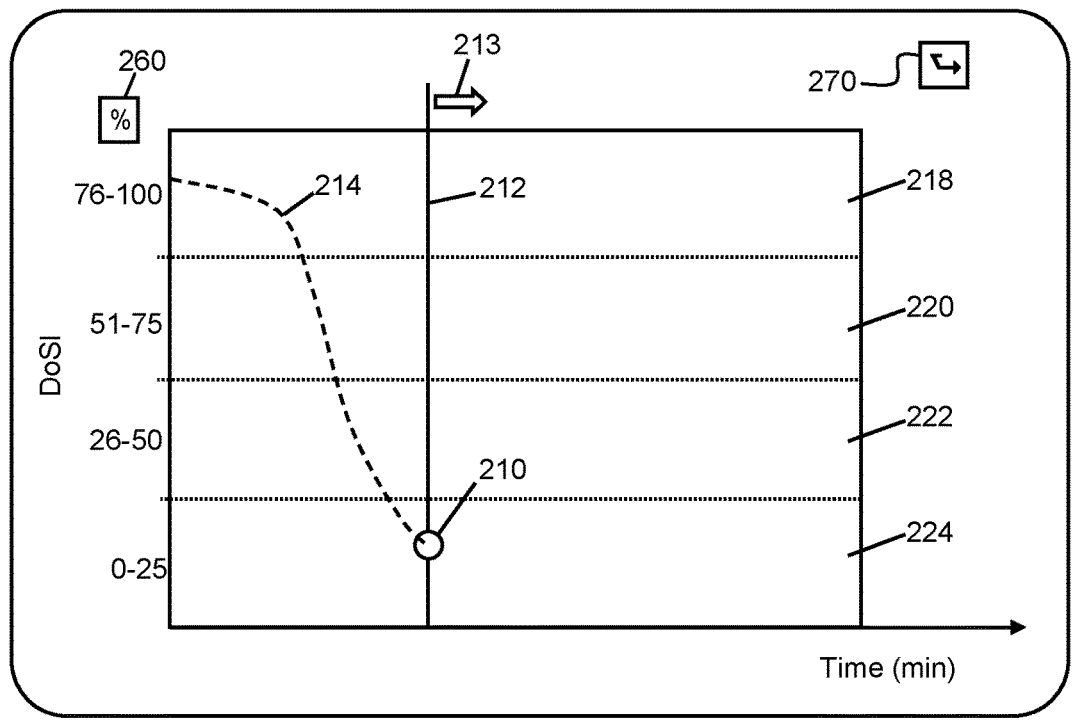
Figure 4B:
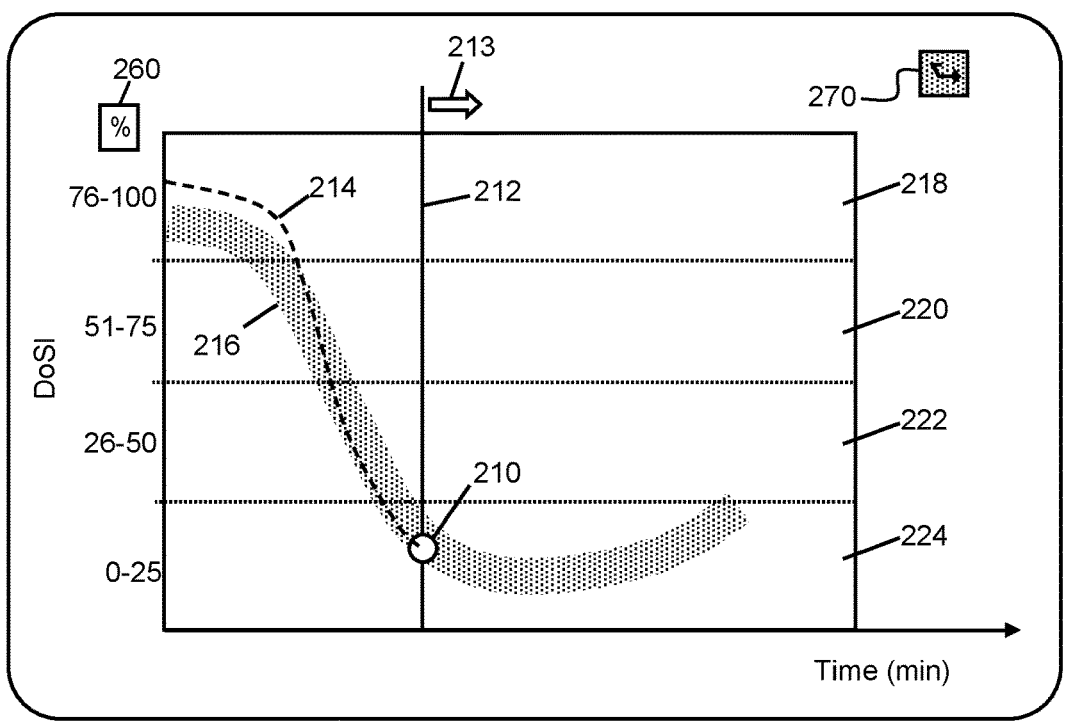

FIGS. 4A and 4B shows a GUI (200, c) that is graphical display of a progress of a treatment session over time (x-axis). Reference is made to the DoSI graph in FIG. 4A; the graph in FIG. 4B contains equivalent features (not labelled). The current DoSI (210) of the subject at the current point of time shown as a circle (210) along a time axis (212) that advances in the direction of arrow (213) as the treatment session progresses. The DoSI graph y-axis displayed is divided into 4 zones: 0-25% (224), 26-50% (222), 51-75% (220), 76-100% (218); these may optionally be coloured to indicate a level of safety (e.g. 76-100%—red, 51-75%—orange, 26-50%—light green, 0-25%—deep green as in FIG. 2.

Historical or trending DoSI for the subject during the treatment session is shown as a dashed line (214). Current units (percent) are indicated (260); the box (260) may also serve as a button to cycle between different units (e.g. to unitless and/or other units). In FIG. 4B, the same graph as FIG. 4A is shown; button (270) is unselected in FIG. 4A and is selected in FIG. 4B. Button (270) toggles on or off a display of expected DoSI (216) for the subject that is superimposed on the graph; current DoSI (210) and historical DoSI (214) can be visually compared with the expected DoSI (216).

Figure 5:
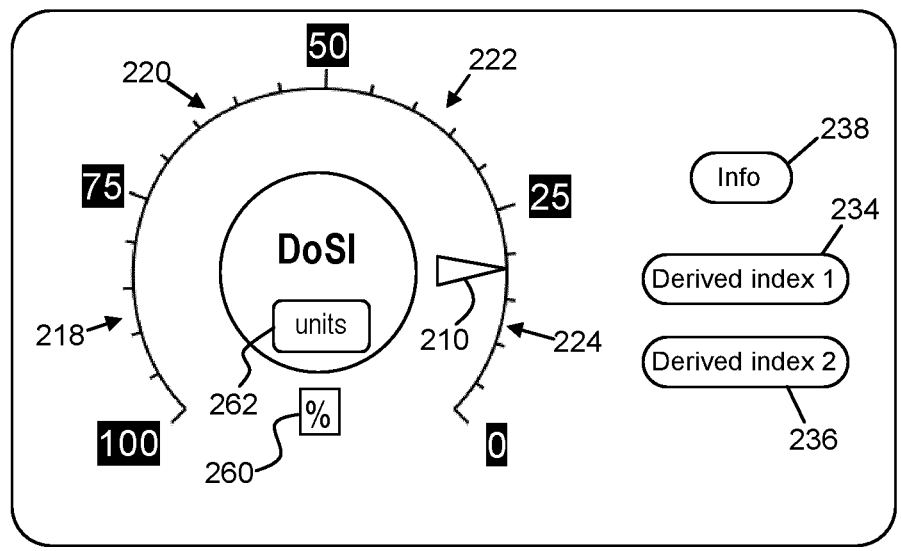

FIG. 5 shows a GUI (200, d) that contains a "speedometer" scale of the current DoSI (210) of the subject shown as a pointer. Current scale units (percent) are indicated (260), that can be changed (e.g. to unitless and/or other units) with a units button (262). The DoSI speedometer scale is divided into 4 zones: 0-25% (224), 26-50% (222), 51-75% (220), 76-100% (218); these may optionally be coloured to indicate a level of safety (e.g. 76-100%-red, 51-75%—orange, 26-50%—light green, 0-25%—deep green as in FIG. 2. Buttons (234, 236, 238) are displayed from which the user can select one or more options to change the display of the GUI and for further information.

Figure 6:
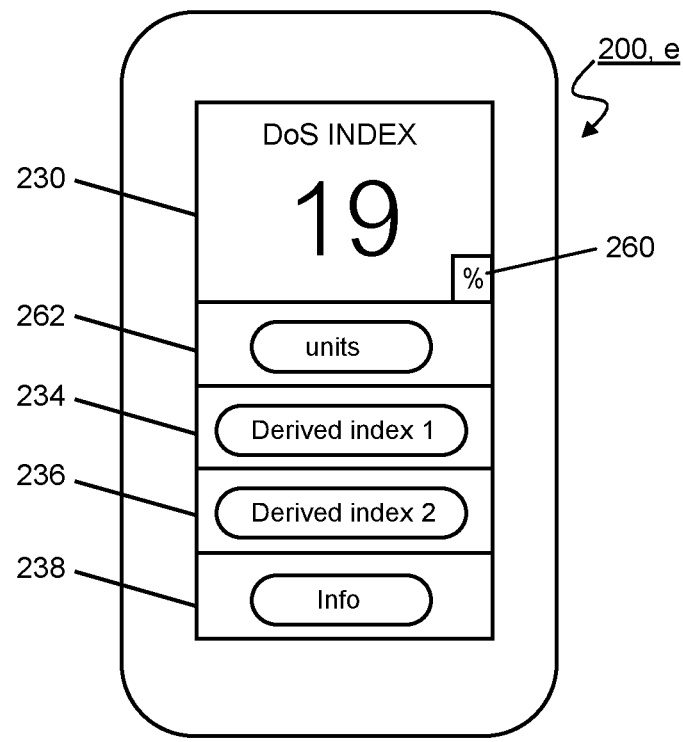

FIG. 6 shows a GUI (200, b) that contains a numerical display of the current DoSI (230) of the subject. Current units (percent) are indicated (260), that can be changed (e.g. to unitless and/or other units) with a units button (262). Buttons (234, 236, 238) are displayed from which the user can select one or more options to change the display of the GUI and for further information.

Figure 7:
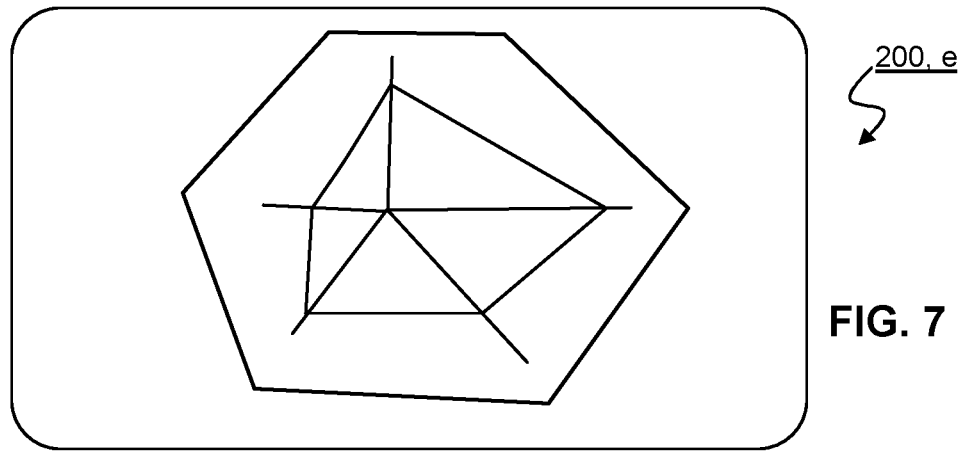

FIG. 7 shows a GUI (200, e) wherein different indexes are represented. External point of each axis represents the maximal scale value for this index. Chart gives an overview of the values of different indexes.

Figure 8:
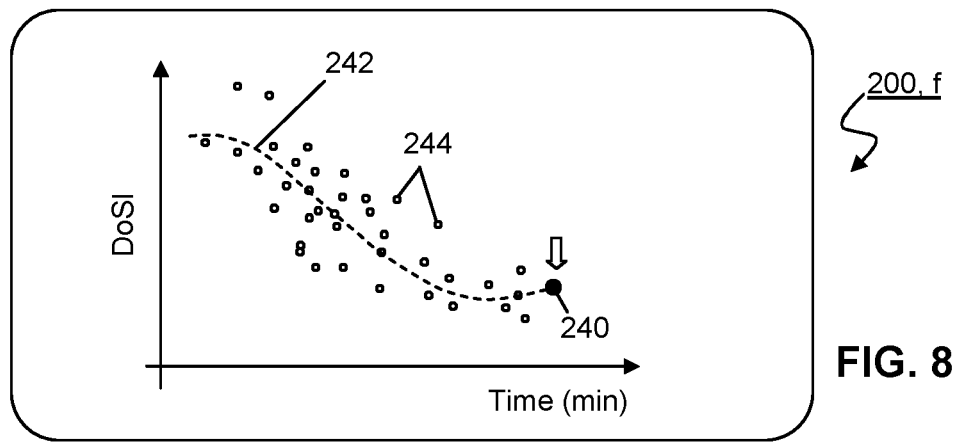

FIG. 8 shows a GUI (200, f) displaying current DoSI for the subject (240) during a therapeutic session over time. Historical or trending datapoints (244) are also shown, and an average of the historical or trending data points is shown as a dashed line (242).

Figure 9:
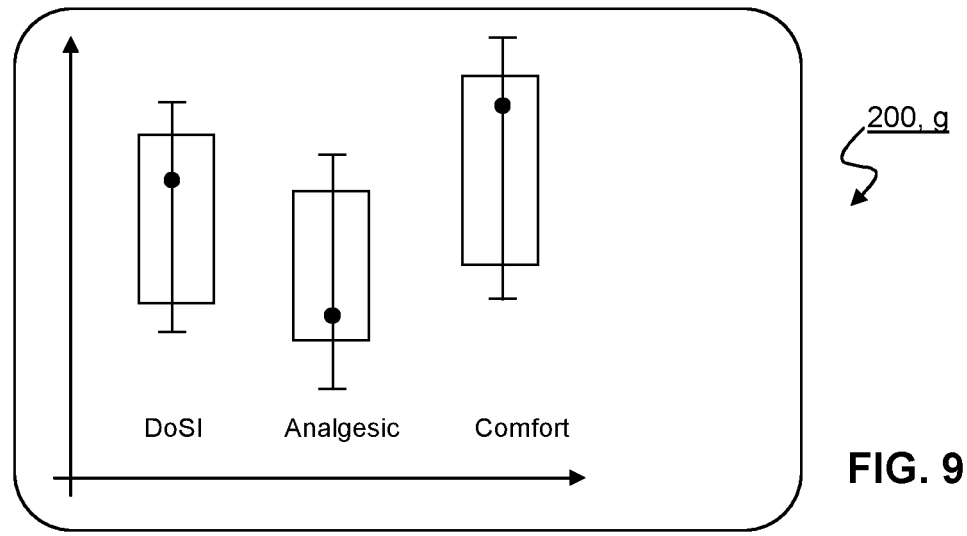

FIG. 9 shows a GUI (200, g) displaying an average measure per index (DoSI, analgesic, comfort) compared to the rest of the population (analytics) at the same point in time of the session.

A system may be provided for determining and/or monitoring a level of modified state of consciousness of a subject receiving the treatment session described herein, the system comprising a monitoring apparatus configured to obtain measured data of the subject. The system may be configured for use in a method described herein. Preferably the monitoring apparatus comprises the EEG capturing unit described below. The monitoring apparatus may be integrated into the wearable device e.g. headset as described below. The system may, but not necessarily, further comprise a media renderer configured for presenting the treatment session to the subject as described below.

A system may be provided for determining and/or monitoring a level of non-pharmacological and/or pharmacological modified state of consciousness of a subject receiving a treatment session, the system comprising:
- optionally media renderer configured for presenting the treatment session to the subject;
- a monitoring apparatus configured to obtained measured data of the subject;
- a controller module configured for receiving measured data from the monitoring apparatus, and transforming the response data comprising the measured data into a depth of state (DoS) index (DoSI) and/or a depth of hypnosis (DoH) index (DoHI), the DoHI and/or DoSI representing a measure of the non-pharmacological and/or pharmacological modified state of consciousness of the subject.

The media renderer presents a treatment session to the subject. The treatment session may contain hypnosis and/or other evidence-based psychological and/or mind/body intervention. The media render may comprise screen (e.g. LED, LCD, projector) on which moving images are displayed. The images immerse the attention of the subject and/or control the subject's experience and physiological response. The media render may comprise a sound transducer (e.g. earphone, headphone, speaker) to which audio is passed (e.g. music, dialogue, sound effects).

The media renderer may be integrated as a wearable device, e.g. headset. The media rendered may be provided as a virtual reality headset, as an augmented reality headset, or mixed reality headset. Most preferably the media renderer is integrated into a wearable device that provides virtual/augmented/mixed/etc. reality; which typically includes a display or projector, stereo sound (mono, stereo, multidimensional), and head motion tracking sensors (e.g. gyroscopes, accelerometers, structured light systems, etc.). Examples of suitable headsets are those supplied by Oculus (e.g. Oculus Rift, Oculus Go), LG electronics (e.g. LG 360 VR), Pico (e.g. G2 4K, G2 Pro), HTC (e.g. HTC Vive), Samsung (e.g. Samsung Gear VR), Google (e.g. Google Cardboard), Microsoft (Hololens), and other off-the-shelf or customised designs. The media renderer may be expanded by also rendering somatosensory content, such as vibrations (e.g. vibration modules equipped in a seat), and/or olfactory content (e.g. releasing one or more fragrances into the nasal cavity). Optionally, the media renderer may be equipped with a computing unit for executing or playing data, or it may receive data from an external media server (i.e. streaming).

The media renderer may be provided as a separate device (e.g. separate smart device, separate sound transducer). The separate device may removably couple with the wearable device described elsewhere herein.

The monitoring apparatus may be configured to capture response data of the subject, in particular measured data of the subject. The monitor apparatus comprises one or more units, each unit containing, depending on the type of unit one or more electrodes, sensors, cameras that capture measured data. The measured data component of each unit may or may not result from a processing of a signal captured by the one or more electrodes, sensors, cameras.

The monitoring apparatus may comprise an electroencephalogram (EEG) capturing unit. The response data i.e. measured data comprises outputted EEG data. EEG capturing unit may comprise at least two (e.g. 2, 3, 4, 5 or more), preferably a plurality of electrodes configured for acquiring electrical activity data from the subject brain. The electrodes may be configured for placement at predetermined positions across the subject's cephalic region; for instance to the frontal, parietal, and/or occipital region. An exemplary electrode configuration is 2 frontal electrodes, 2 lateral electrodes, 1 occipital electrode with respect to the head.

In a preferred configuration, the EEG capturing unit may comprise:
- at least one frontal EEG electrode (F-EEG electrode) configured for attachment to or contact with the scalp anatomical region corresponding to the frontal lobe;
- at least one parietal EEG electrode (P-EEG electrode) configured for attachment to or contact the scalp anatomical region corresponding to the parietal lobe.

The EEG capturing unit may further comprise a ground or reference electrode. This is situated away from the F- or P-EEG electrode to allow spatial reconstruction.

The electrodes may be integrated into a wearable device e.g. wearable headset. The electrodes may be fixed to or detachable from the wearable device. The electrodes may be dry-contact electrodes. The electrodes may be held in place be gravity, or by a force (e.g. applied by a spring or elastic) or by adhesive. The electrodes may be reusable or one-time use. The electrodes may be integrated into a head-strap or fixing band. The electrodes may be integrated into a mask portion of the media renderer. The electroencephalogram (EEG) capturing unit typically includes an amplifier for amplification of the detected signal. Signals are digitised for processing by a digital-to-analogue converter for processing by the processing unit. The sampling rate is typically at least 2.5 times higher than the highest frequency of interest. The digital-to-analogue converter may be separate or built into the processing unit.

The monitoring apparatus may comprise an electromyography (EMG) capturing unit. The response data i.e. measured data comprises outputted EMG data. EMG capturing unit may comprise at least one (e.g. 1, 2, 3, 4, 5 or more), preferably a plurality of electrodes configured for acquiring electrical activity data from the subject muscle tissue. Where an EEG capturing unit is present, the EMG capturing unit may share an electrode with the EEG capturing unit. The electrodes may be configured for placement at predetermined positions across the subject's cranial and/or facial region; preferably to the frontal region.

The electrodes may be integrated into a wearable device e.g. wearable headset. The electrodes may be fixed to or detachable from the wearable device. The electrodes may be dry-contact electrodes. The electrodes may be held in place be gravity, or by a force (e.g. applied by a spring or elastic) or by adhesive. The electrodes may be reusable or one-time use. The electrodes may be integrated into a head-strap or fixing band. The electrodes may be integrated into a mask portion of the media renderer. The EMG capturing unit typically includes an amplifier for amplification of the detected signal. Signals are digitised for processing by a digital-to-analogue converter for processing by the processing unit. The digital-to-analogue converter may be separate or built into the processing unit.

The monitoring apparatus may comprise a respiratory data (RD) capturing unit. The response data i.e. measured data comprises outputted respiratory data. RD capturing unit may comprise at least one (e.g. 1, 2, 3, 4, 5 or more) sensor(s) configured for acquiring RD from the subject. The respiratory data may comprise one or more of respiration rate, respiration rate variability, inhalation pressure. The RD capturing unit may comprise one or more photoplethysmogram (PPG) sensors. A PPG sensor detects blood volume changes in vasculature below the skin; the sensor is typically optical. The respiration rate and respiration rate variability may be determined from the PPG sensor. A PPG sensor may be placed at temple area and/or forehead area, and/or at a peripheral location. A peripherally-located sensor may communicate with the controller module and/or RD capturing unit using a wired or wireless communication. The respiration rate and respiration rate variability may be determined from the PPG sensor. The RD capturing unit may utilise signals capture from one or more ECG electrodes placed at location where respiratory rate is detectable. One or more of the sensor(s) may be configured for placement at predetermined positions across the subject's cranial and/or facial region. The sensor(s) may be integrated into a wearable device e.g. wearable headset. The sensor(s) may be fixed to or detachable from the wearable device. The sensor(s) may be dry-contact sensor(s) and/or electrode(s). The sensor(s) may be held in place be gravity, or by a force (e.g. applied by a spring or elastic) or by adhesive. The sensor(s) may be reusable or one-time use. The sensor(s) may be integrated into a head-strap or fixing band. The sensor(s) may be integrated into a mask portion of the media renderer e.g. so as to place PPG sensors at the forehead and/or temple region. The RD capturing unit may comprise a wearable chest band containing a force transducer that measures the expansion and contraction of the chest; the respiration rate and respiration rate variability may be determined from the wearable chest band sensor. The RD capturing unit may comprise an airways air pressure detector that measures the air pressure (e.g. during inhalation or exhalation). The RD capturing unit typically includes an amplifier for amplification of the detected signal. Signals are digitised for processing by a digital-to-analogue converter for processing by the processing unit. The digital-to-analogue 5 converter may be separate or built into the processing unit.

The monitoring apparatus may comprise a heart rate (HR) capturing unit. The response data i.e. measured data comprises outputted HR data. HR capturing unit may comprise at least one (e.g. 1, 2, 3, 4, 5 or more) sensor(s) and/or electrode(s) configured for acquiring heart data from the subject. The HR capturing unit may comprise one or more photoplethysmogram (PPG) sensors that detects blood volume changes vasculature below the skin; the sensor is typically optical. A PPG sensor may be placed at temple area and/or forehead area. The peaks of a captured PPG wave can be estimate the heart rate, heart rate variability as well as heartbeat interval, and blood pressure (two PPG sensors). The HR capturing unit may comprise one or more ECG electrodes configured for acquiring electrical activity data from the subject heart. Where an EEG or EMG capturing unit is present, the HR capturing unit may share an electrode with the EEG or EMG capturing unit. One or more of the sensor(s) and/or electrode(s) may be configured for placement at predetermined positions across the subject's cranial and/or facial region; they may be placed bilaterally. Where the sensors are PPG sensors, may be configured for placement at the forehead and/or temple region. The sensor(s) and/or electrode(s) may be integrated into a wearable device e.g. wearable headset. The sensor(s) and/or electrode(s) may be fixed to or detachable from the wearable device. The sensor(s) and/or electrode(s) may be dry-contact sensor(s) and/or electrode(s). The sensor(s) and/or electrode(s) may be held in place be gravity, or by a force (e.g. applied by a spring or elastic) or by adhesive. The sensor(s) and/or electrode(s) may be reusable or one-time use. The sensor(s) and/or electrode(s) may be integrated into a head-strap or fixing band. The sensor(s) and/or electrode(s) may be integrated into a mask portion of the media renderer e.g. so as to place PPG sensors at the forehead and/or temple region. The HR capturing unit typically includes an amplifier for amplification of the detected signal. Signals are digitised for processing by a digital-to-analogue converter for processing by the processing unit. The digital-to-analogue converter may be separate or built into the processing unit.

The monitoring apparatus may comprise an electrooculography (EOG) capturing unit. The response data i.e. measured data comprises outputted EOG data. EOG capturing unit may comprise at least one (e.g. 1, 2, 3, 4, 5 or more), preferably a plurality of electrodes configured for acquiring electrical activity data from around the subject eye. Where an EEG or EMG capturing unit is present, the EOG capturing unit may share an electrode with the EEG or EMG capturing unit. The electrode(s) may be configured for placement at predetermined positions across the subject's cranial and/or facial region; preferably to the around (e.g. above and below, to left and right of an eye). The electrode(s) may be integrated into a wearable device e.g. wearable headset. The electrode(s) may be fixed to or detachable from the wearable device. The electrode(s) may be dry-contact electrode(s). The electrode(s) may be held in place be gravity, or by a force (e.g. applied by a spring or elastic) or by adhesive. The electrode(s) may be reusable or one-time use. The electrode(s) may be integrated into a head-strap or fixing band. The electrode(s) may be integrated into a mask portion of the media renderer. The EOG capturing unit typically includes an amplifier for amplification of the detected signal. Signals are digitised for processing by a digital-to-analogue converter for processing by the processing unit. The digital-to-analogue converter may be separate or built into the processing unit.

The monitoring apparatus may comprise an electrodermal activity (EDA) capturing unit. The response data i.e. measured data comprises outputted EDA data. EDA capturing unit may comprise at least one (e.g. 1, 2, 3, 4, 5 or more), preferably a plurality of electrodes configured for acquiring electrical activity data from the subject skin tissue. Where an EEG or EMG capturing unit is present, the EDA capturing unit may share an electrode with the EEG or EMG capturing unit. The electrode(s) may be configured for placement at predetermined positions across the subject's cranial and/or facial region; preferably to the frontal region.

The electrode(s) may be integrated into a wearable device e.g. wearable headset. The electrode(s) may be fixed to or detachable from the wearable device. The electrode(s) may be held in place be gravity, or by a force (e.g. applied by a spring or elastic) or by adhesive. The electrode(s) may be reusable or one-time use. The electrode(s) may be integrated into a head-strap or fixing band. The electrode(s) may be integrated into a mask portion of the media renderer. The EDA capturing unit typically includes an amplifier for amplification of the detected signal. Signals are digitised for processing by a digital-to-analogue converter for processing by the processing unit. The digital-to-analogue converter may be separate or built into the processing unit.

The EDA capturing unit may be configured for measurement of galvanic skin response. The response data i.e. measured data comprises outputted GSR data. EDA capturing unit may comprise at least one (e.g. 1, 2, 3, 4, 5 or more), preferably a plurality of GSR electrodes configured for acquiring galvanic skin response. Where an EEG or EMG capturing unit is present, the EDA capturing unit may share a localised or reference electrode with the EEG or EMG capturing unit for acquiring galvanic skin response. The electrode(s) may be configured for placement at predetermined positions across the subject's cranial and/or facial region; preferably to the frontal or forehead region. The GSR electrode(s) may be integrated into a wearable device e.g. wearable headset. The GSR electrodes may be fixed to or detachable from the wearable device. The GSR electrodes may be dry-contact electrode(s). The GSR electrode(s) may be held in place be gravity, or by a force (e.g. applied by a spring or elastic) or by adhesive. The GSR electrode(s) may be reusable or one-time use. The GSR electrode(s) may be integrated into a head-strap or fixing band. The GSR electrode(s) may be integrated into a mask portion of the media renderer.

The monitoring apparatus may comprise an electrocardiogram (ECG) capturing unit. The response data i.e. measured data comprises outputted heart rate or ECG data. ECG capturing unit may comprise at least one (e.g. 1, 2, 3, 4, 5 or more), preferably a plurality of electrodes configured for acquiring electrical activity data from the subject heart. Where an EEG, EMG, or EDA capturing unit is present, the ECG capturing unit may share an electrode with the EEG, EMG, or EDA capturing unit. The electrodes being configured for placement at predetermined positions across the subject's chest. The electrodes may be integrated into a wearable device e.g. wearable headset. The electrodes may be fixed to or detachable from the wearable device. The electrodes may be held in place by gravity, or by a force (e.g. applied by a spring or elastic) or by adhesive. The electrodes may be reusable or one-time use. An electrode may be integrated into a head-strap or fixing band. An electrode may be integrated into a mask portion of the media renderer.

The monitoring apparatus may further comprise a physiological monitoring unit. The response data i.e. measured data comprises outputted physiological data. The physiological monitoring unit may comprise at least one (e.g. 1, 2, 3, 4 or more) sensor for acquiring subject's physiological data, in particular a component of the physiological data. The physiological data may relate to one or more of the following: pulse rate, heart rate, heart rate variation, blood pressure, respiration rate, respiration rate variability, inhalation pressure, exhalation pressure, brain oxygenation, blood $O_2$ saturation ($SpO_2$), regional and/or central blood $O_2$ saturation, skin conductance, galvanic skin response, body temperature. The physiological data may relate to one or more of the following: respiration rate, respiration rate variability, inhalation pressure, heart rate.

The monitoring apparatus may comprise a $SpO_2$ capturing unit. The response data i.e. measured data comprises outputted $SpO_2$ data. $SpO_2$ capturing unit capturing unit may comprise at least one (e.g. 1, 2, 3, 4, 5 or more) sensor(s) configured for capturing $SpO_2$ (blood oxygen saturation) data from the subject. The $SpO_2$ data capturing unit may comprise one or more sensors e.g. photoplethysmogram (PPG) sensor; the sensor is typically optical. A sensor may be placed at temple area and/or forehead area. The sensor may be configured for placement at the forehead and/or temple region. The sensor(s) may be integrated into a wearable device e.g. wearable headset. The sensor(s) may be fixed to or detachable from the wearable device. The sensor(s) may be dry-contact sensor(s). The sensor(s) may be held in place be gravity, or by a force (e.g. applied by a spring or elastic) or by adhesive. The sensor(s) may be reusable or one-time use. The sensor(s) may be integrated into a head-strap or fixing band. The sensor(s) may be integrated into a mask portion of the media renderer e.g. so as to place sensor(s) at the forehead and/or temple region. The $SpO_2$ capturing unit capturing unit typically includes an amplifier for amplification of the detected signal. Signals are digitised for processing by a digital-to-analogue converter for processing by the processing unit. The digital-to-analogue converter may be separate or built into the processing unit.

The one or more sensors may be integrated into a wearable device e.g. wearable headset. The one or more sensors may be fixed to or detachable from the wearable device. The one or more sensors may be held in place be gravity, or by a force (e.g. applied by a spring or elastic) or by adhesive. The one or more sensors may be reusable or one-time use. The one or more sensors may be integrated into a head-strap. The sensors may be integrated into a mask portion of the media renderer.

The monitoring apparatus may further comprise a body motion tracking unit. The response data i.e. measured data comprises outputted body motion tracking data. The body motion tracking unit may comprise at least one (e.g. 1, 2, 3, 4 or more) motion sensor for acquiring subject's body motion, in particular a component of the body motion tracking data. Examples of motion sensors include a 2- or 3-axis accelerometer, a gyroscope, one or more cameras, magnetic/induction transducers. The body motion includes movements of the head, limb (arms, legs, hands, knee, elbow). The body motion tracking unit may be a head tracking unit.

The one or more motion sensors may be integrated into a wearable device e.g. wearable headset. The one or more motion sensors may be fixed to or detachable from the wearable device. The one or more motion sensors may be held in place be gravity, or by a force (e.g. applied by a spring or elastic) or by adhesive. The one or more motion sensors may be reusable or one-time use. The one or more motion sensors may be integrated into a head-strap. The motion sensors may be integrated into a mask portion of the media renderer.

The monitoring apparatus may further comprise an eye-tracking unit. The response data i.e. measured data comprises outputted eye tracking data. The eye tracking unit may comprise at least one (e.g. 1, 2, 3, 4 or more) camera for monitoring movement of one or both eyes of the subject. The eye tracking unit may comprise at least one light source (e.g. visible, infrared) configured to illuminate the eye. Captures images may be analysed using eye tracking software to determine subject's focus of attention, drowsiness, consciousness or other mental states.

The one or more cameras may be integrated into a wearable device e.g. wearable headset. The one or more cameras may be fixed to or detachable from the wearable device. The one or more cameras may be integrated into a mask portion of the media renderer.

The monitoring apparatus may further comprise a facial expression capturing unit. The response data i.e. measured data comprises outputted facial expression data—e.g. emotions, nociception. The facial expression capturing unit may comprise at least one (e.g. 1, 2, 3, 4 or more) camera for monitoring facial expressions of the subject. The facial expression capturing unit may comprise at least one light source (e.g. visible, infrared) configured to illuminate the face. Captures images may be analysed using facial expression recognition software to determine subject's facial expressions and responses.

The one or more cameras may be integrated into a wearable device e.g. wearable headset. The one or more cameras may be fixed to or detachable from the wearable device. The one or more cameras may be integrated into a mask portion of the media renderer.

The monitoring apparatus may comprise an EEG capturing unit, an EMG capturing unit, an EDA capturing unit, an ECG capturing unit, a physiological monitoring unit, a head tracking unit, an eye tracking unit and a face capturing unit. The monitoring apparatus may comprise an EEG capturing unit, an EMG capturing unit, a HR capturing unit, and respiratory data capturing unit.

The monitoring apparatus may be integrated into the wearable device e.g. headset. One or more electrodes and/or one more sensors, and/or one more cameras of the monitoring apparatus may be integrated into the wearable device. Preferably the monitoring apparatus comprises the EEG capturing unit described herein having at least one F-EEG electrode and optionally at least one P-EEG electrode. The F-EEG electrode may be placed on a mask part of a wearable device or on a strap. The mask part may be closed (e.g. when supporting a virtual reality viewer) or open (e.g. when virtual reality viewer is absent).

The wearable device may comprise no sound transducer and no built-in screen. The screen and/or sound may be supplied via another device e.g. earphones and/or smart device. The wearable device may comprise a coupling for the smart device. With the absence of sound transducer and no built-in screen, the treatment session may be delivered by a hypnotist or hypnotherapist.

The wearable device may comprise a sound transducer (e.g. earphone, headphone, speaker) and not a built-in screen. The screen may be supplied via a smart device. The wearable device may comprise a coupling for the smart device The wearable device may comprise a combination of build-in sound transducer (e.g. earphone, headphone, speaker) and a built-in screen.

Figure 10A:
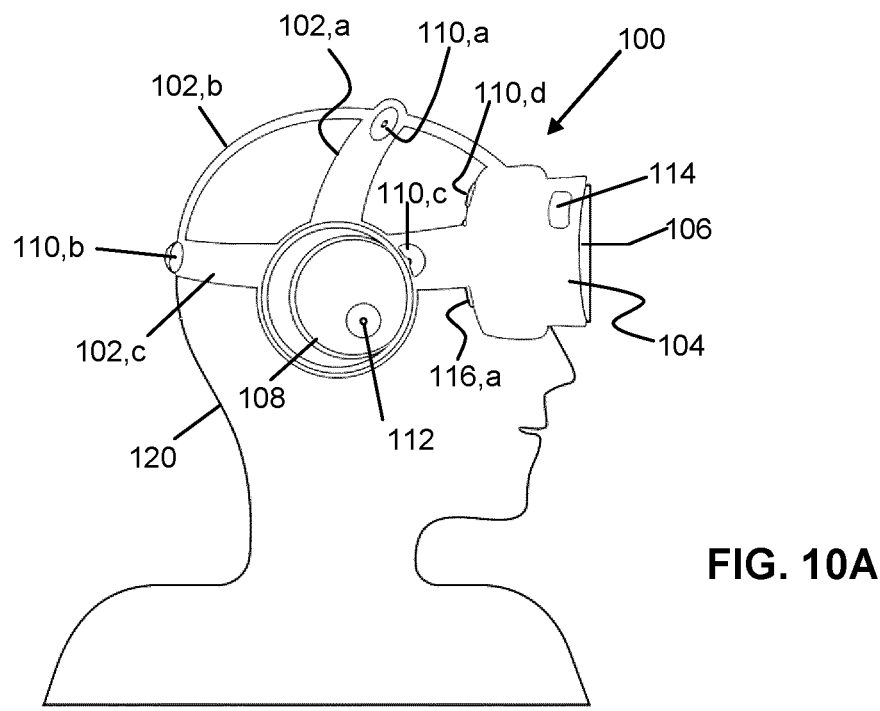
FIG. 10A illustrates a wearable device incorporating an eye-mask incorporating a media renderer, electrodes and sensors.
Figure 10B:
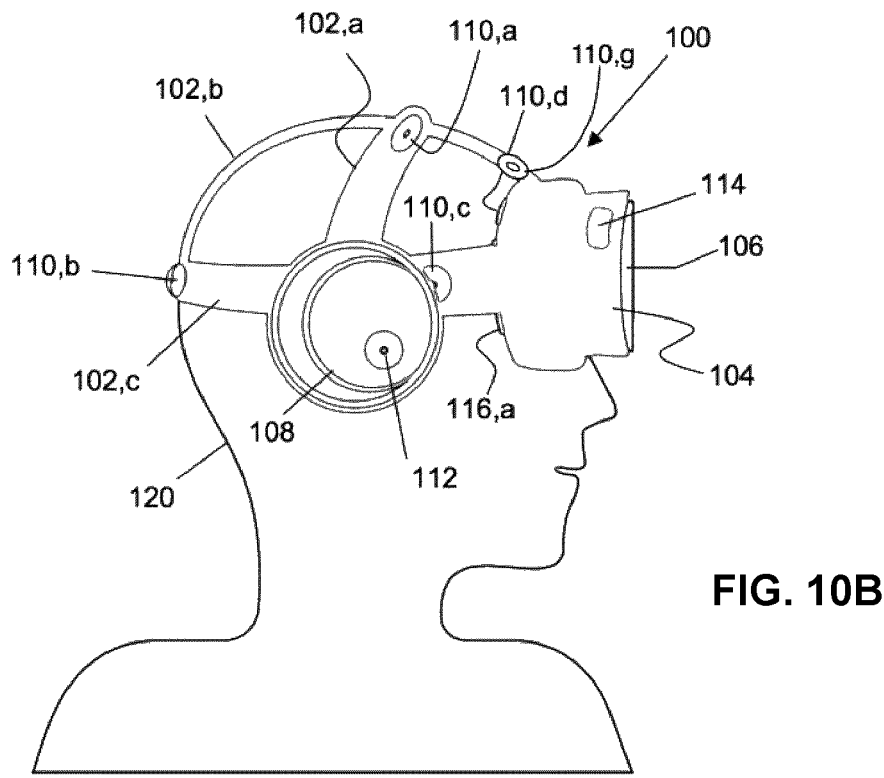
FIG. 10B is similar to FIG. 10A with the inclusion of a frontal (F) EEG electrode for measurement of EEG data.
Figure 10C:
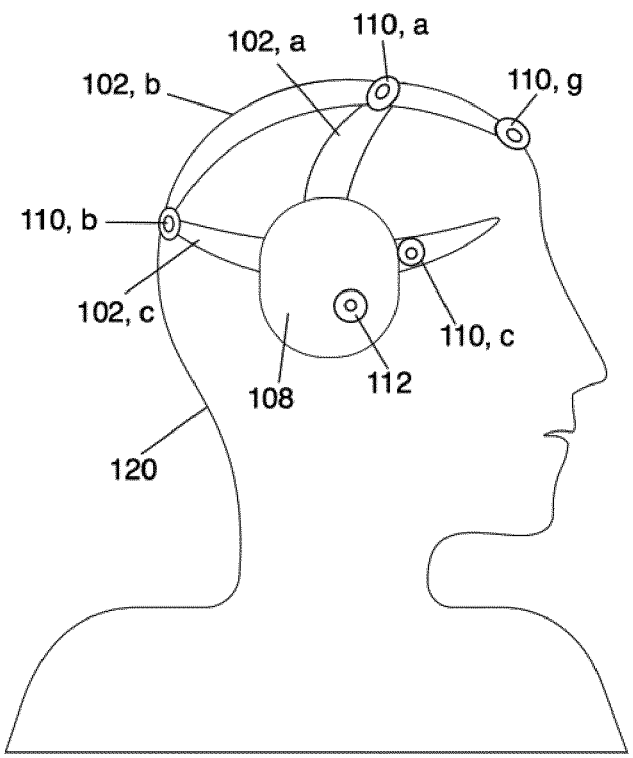
FIG. 10C is similar to FIG. 10B devoid of a virtual reality viewer, headphones are present.
Figure 10D:
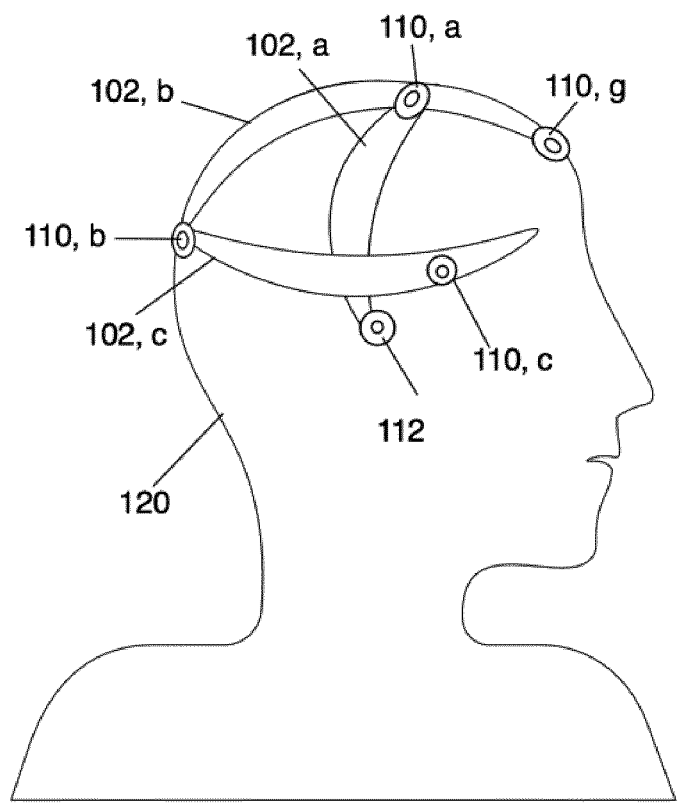
FIG. 10D is similar to FIG. 10B devoid of a virtual reality viewer and headphones.
Figure 11:
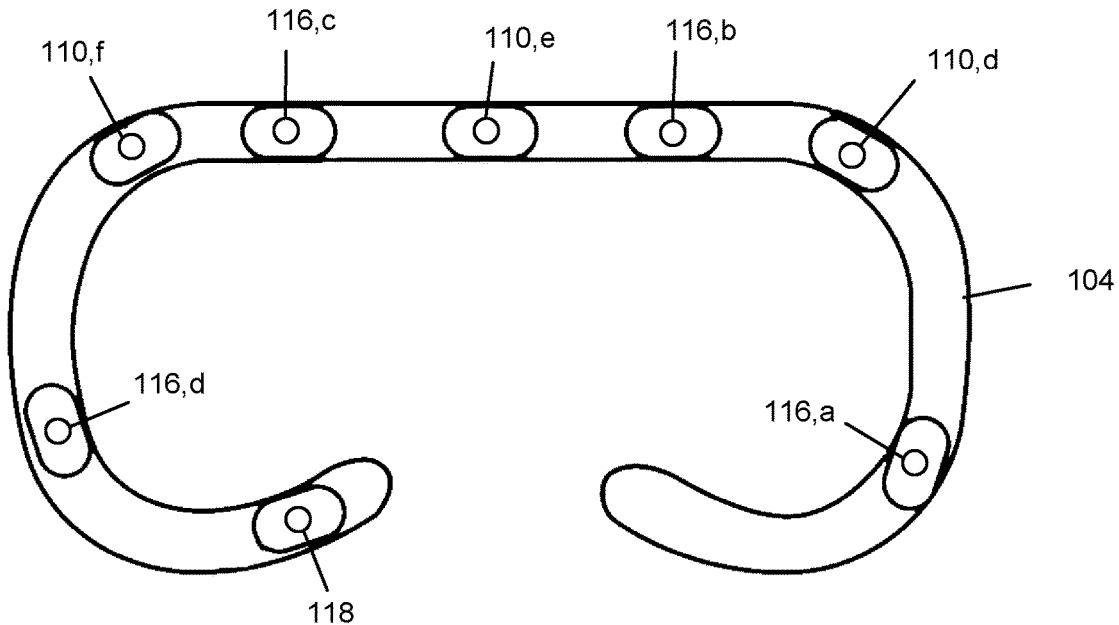
FIG. 11 illustrates a rim of the eye-mask of the wearable device disposed with electrodes.

An example of a wearable device is given in FIGS. 10A to D and 11. FIGS. 10A to 10D depicts a wearable device (100). The wearable device (100) comprises a plurality of straps (102,a,b,c) that hold the wearable device (100) in position on the head (120) of the subject. The straps may be elasticated or non-elasticated. The straps (102,a,b,c) also hold a plurality of electrodes and/or sensors in position on the head (120) of the subject. Depicted in FIGS. 10A to D are electrodes (110, a (central (C) EEG electrode), b (parietal (P) EEG electrode), c (temporal), for measurement of EEG data; sensor (112) for measurement of heart rate, heart rate variation, SPO$_2$. FIGS. 10A and B further depict electrode 110, d (prefrontal right) for measurement of EEG data. FIGS. 10B to D further shows electrode g (frontal (F) EEG electrode) for measurement of EEG data. In FIGS. 10A and 10B, an eye mask (104) is provided that supports a virtual reality viewer (106) and headphones (108) (media renderer) in position on the head (120) of the subject. In FIG. 10C, the virtual reality viewer is absent, but the headphones (108) (media renderer) are present and positioned over the ears of the subject by the straps. In FIG. 10D, the virtual reality viewer and eye mask and headphones (108) are absent; the treatment session may be provided externally. FIG. 11 is a view of an exemplary face-contacting edge of the mask (104) disposed with electrodes (116, a, b, c, d) (110, d, e, f) for measurement of EEG data; electrode (118) for measurement of skin conductance.

Electrode 110, e may be a prefrontal in the sagittal plane EEG electrode, Electrode 110, f may be a prefrontal left EEG electrode.

Figure 12:
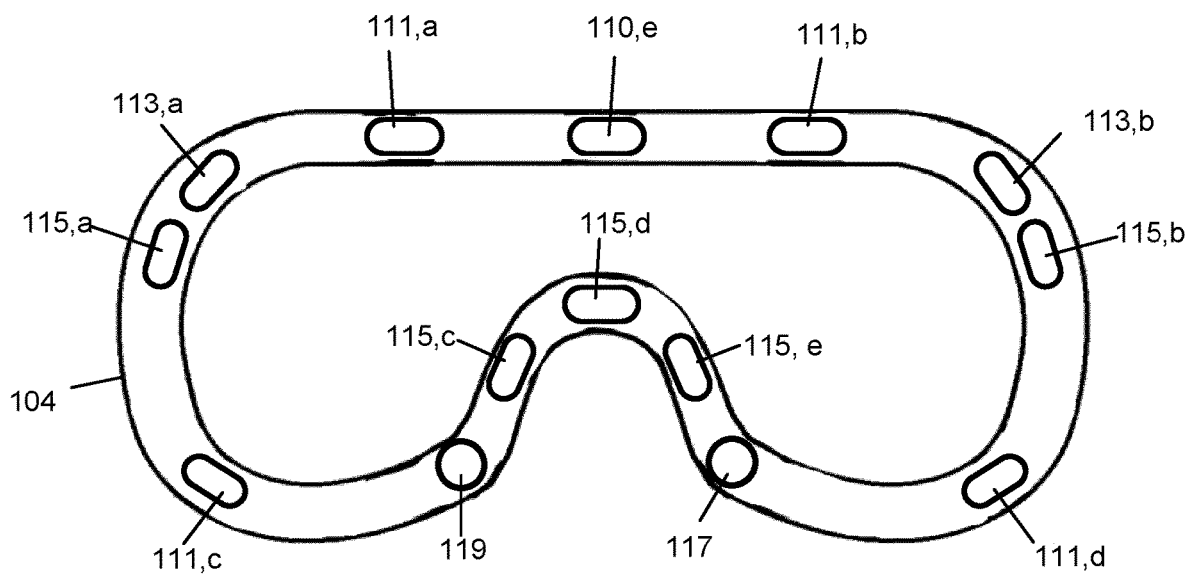
FIG. 12 illustrates rim of the eye-mask of the wearable device disposed with another configuration of electrodes and sensors.

FIG. 12 is a view of another exemplary face-contacting edge of the mask (104) disposed with
- a pre-frontal EEG electrode (110e) in the sagittal plane for measurement of EEG data (may optionally be disposed on an extension extending in a superior direction, for instance on a head strap);
- EMG electrode (111a to 111 d) for measurement of EMG data;
- PPG sensors (113a, 113b) for measurement of respiratory data, heart rate data, blood pressure, spO$_2$;
- EOG electrodes (115a to 115e) for measurement of EOG data;
- GSR electrode (117) for measurement of GSR data;
- ground electrode (119) that can act a reference/ground electrode in combination with one or more of the EEG (110e), EMG (111a to 111d), EOG (115a to 115e), GSR (117) electrodes.

The controller module may be configured for receiving measured data from the monitoring apparatus, and transforming the response data into the level of modified state of consciousness of a subject.

The controller module may be configured for receiving measured data from the monitoring apparatus, and transforming the response data comprising the measured data into one or more of DoDI DoHI, DoSI. The evaluation protocol may comprise use of one or more of a mathematical (e.g. statistical) model, trained machine-leaning model, mathematical index, reference data.

The controller module may be configured for receiving measured data from the monitoring apparatus, and transforming the response data comprising the measured data into the DoSI and/or DoHI representing a measure of the non-pharmacological and optionally pharmacological modified state of consciousness of the subject, using an evaluation protocol as described elsewhere herein. The evaluation protocol may comprise use of one or more of a mathematical (e.g. statistical) model, trained machine-leaning model, mathematical index, reference data.

The controller module typically comprises a circuit (e.g. microprocessor) configured to perform processing steps and memory. The controller module may or may not be integrated into a wearable device. The controller may be at least partly integrated into the wearable device. The controller may be at least partly integrated into a smart device (e.g. smartphone, tablet).

The method may be a computer implemented method. Provided is a computing device or system configured for performing the method as described herein.

Provided is a computer program or computer program product having instructions which when executed by a computing device or system cause the computing device or system to perform the method as described herein.

Provided is a computer readable medium having stored thereon instructions which when executed by a computing device or system cause the computing device or system to perform the method as described herein.

Provided is a data stream which is representative of a computer program or computer program product having instructions which when executed by a computing device or system cause the computing device or system to perform the method as described herein.

The method and system described herein enable the therapist to quantify the patients state or hypnotic state, enable optimal and potentially individual titration of initial dosages of anxiolytics; . . . hypnotics, optimize non-pharmacological eventually combined sedation (VR therapy titration); provide safer progress by Quantifying, Visualizing, Trending and potentially predict patient's physiological reaction/level of comfort during clinical, medical or therapeutic interventions; increase subject safety; increase subject amnesia of medical intervention.

Also provided is use of a computer-implement method described herein for determining a level of sedation of a subject induced non-pharmacologically. The sedation may be for a an intervention e.g. replacing and/or supplementing a pharmacological anaesthetic with a non-pharmacological anaesthetic. The intervention may be any including curative, and/or ameliorative, and/or diagnostic. The intervention may be invasive (e.g. surgical, endoscopic, catheterisation) or non-invasive (e.g. medical image acquisition, radiotherapy).

Also provided is a use of computer-implement method described herein for anxiety management before an intervention.

Also provided is a use of computer-implement method described herein for management of chronic symptoms.

Also provided is a use of computer-implement method described herein for management of post-operative or post-intervention symptoms.

Experimental Data

In a study with 12 healthy subjects volunteers (10 included in the analysis), the modified state of consciousness during a hypnotic treatment session was measured by self-reporting of the subject using a validated questionnaire presented after the treatment session. The hypnotic session was delivered using a virtual reality headset. The hypnotic package used was Sedakit (Aqua 30 minute module which uses clinical hypnosis and respiration-altering techniques). At certain moments during the hypnotic treatment session, each subject was exposed to a transcutaneous electrical stimulus. Each subject was asked to rate at least dissociation as they perceived it during the hypnotic treatment session. During the hypnotic treatment session, electroencephalogram (EEG) measured data was collected from each subject. For the EEG measurements, EEG electrodes were used placed so as to cover the scalp and so as to detect local voltage fluctuations resulting localised regions of the brain. A high density EEG was employed with 256 channels. Electrodes were placed according to the predefined layout for 256-channel Hydrocel Geodesic Sensor Network. The results show measurable and statistically significant effect of the hypnotic treatment session regarding dissociation increase (Tables 1 and 2).

TABLE 1

Wicoxon signed-rank test
Overview of results: self-reported data for subjects with and without hypnotic treatment session.

| Self-reported state | Normal awake state Mean ± SD Median [IQR] | Hypnotic treatment session Mean ± SD Median [IQR] | p-value | Adjusted p-value (Bonferroni correction) |
|---|---|---|---|---|
| Dissociation | 4.11 (3.13) 4.95 [5.72] | 7.52 (1.43) 8 [0.9] | 0.0032 | 0.0162 |

TABLE 2

Spearman correlation for dissociation and stimulation intensity.

|  | Dissociation |
|---|---|
| Stimulation Intensity | rs = 0.471 p = 0.019 |

The r is the general correlation coefficient. The rs is the spearman correlation coefficient. It can take a range of values from +1 to −1. A value of 0 indicates that there is no association between the two variables. A value greater than 0 indicates a positive association; that is, as the value of one variable increases, so does the value of the other variable. A value less than 0 indicates a negative association; that is, as the value of one variable increases, the value of the other variable decreases. The p is the p-value associated with the statistical test to evaluate whether the correlation is statistically significant and not just a coincidence. Generally, a p-value smaller than 0.05 is considered as statistically significant (closer to zero, the best).

Results from the EEG analysis allowed associations to made between localised brain structures/networks and dissociation under hypnosis. Identification of those localised structures/networks associated with dissociation allows objective monitoring of the level of modified state of consciousness of the subject during a hypnotic treatment session, as a link between level of modified state of consciousness of the subject and dissociation is known.

Time-domain EEG analysis showed overall decreased in the ERP (event related potential) components during whilst in an hypnotic state compare to normal awake eye open state. There was a difference in overall mean signal peak-to-peak amplitude (MSPA) time-locked to the electrical stimulus onset. The difference in ERP amplitude between the 2 groups with and without hypnotic treatment) was found to be significant at a measurement location of the frontal lobe (F) (frontal midsagittal plane intersection: decrease in overall signal amplitude ("less involved in the response"). This study is the first one showing significant MSPA changes at this specific location when comparing a modified state of consciousness (non-pharmacologically e.g. hypnotically induced) to a normal awake state.

Specifically, we extracted the mean signal peak-to-peak amplitude (MSPA) for electrode F, and obtained the following results:

The MSPA is significantly lower during the hypnotic session at electrode locations F (−24.13 with no hypnosis vs −11.16 with hypnosis, p-value=0.019);

The self-reported measure of dissociation is correlated (spearman) with the MSPA at electrode location F (rs=−0.41, p=0.07). FIG. 14 shows a graph indicating the correlation between MSPA measured at the EEG F-electrode and dissociation.

In the brain, several processes occur at the same time (parallel processing). Each process is expressed in a specific frequency range using, we were able to explore the different processes by transforming the time domain signals (e.g. by fast Fourier transform) into the frequency domain. From the frequency domain signals the power of a specific signal frequency band can be determined, where power refers to a square of amplitude of the frequency domain signals within a specified in a frequency range (e.g. delta-theta range).

This study is the first one showing significant power changes at those specific locations when comparing a modified state of consciousness (non-pharmacologically e.g. hypnotically induced) to a normal awake state. We found significant power differences between the subject in the modified state of consciousness (non-pharmacologically hypnotically induced) to a normal awake state when extracting power at a certain frequency band. In particular we observed a decrease under hypnosis in the band within the delta-theta (dt) frequency range, located around the frontal lobe (F) and Parietal lobe (P) (early component). Early component refers to the power decrease measured from 0.1 to 0.5 sec after the electrical stimulus onset.

The results are the first identifying location-specific brain frequency band differences induced by hypnosis.

Specifically, we extracted the power for a band within the delta-theta (dt) frequency range at electrodes F and P, and obtained the following results:

The power associated with the dt frequency band range was significantly lowered by hypnosis at the 2 electrodes location P (0.84 with no hypnosis vs 0.44 with hypnosis, p=0.027) and F (1.01 with no hypnosis vs 0.43 with hypnosis, p=0.048);

The self-reported measure of dissociation was correlated (spearman) with power in the dt frequency band range at electrodes P (rs=−0.37, p=0.011) and F (rs=−0.55, p=0.010).

FIG. 15 shows correlation between self-reported dissociation and computed power in the dt frequency band range at EEG electrodes F, P.

The invention claimed is:

1. A computer-implemented method for determining and/or monitoring a level of modified state of consciousness of a subject receiving a treatment session, the method comprising the steps of:
    modifying the state of consciousness of the subject non-pharmacologically by presenting the treatment session to the subject, providing the subject with a level of non-pharmacologically modified state of consciousness, wherein modifying the state of consciousness non-pharmacologically comprises bringing the subject to an altered state of consciousness characterized by full or partial dissociation,
    measuring response data being a subject's response to the treatment session, wherein the response data comprises measured data comprising electroencephalogram, EEG data, the EEG data comprising:
    data collected from at least one of:
        at least one frontal (F) EEG electrode located on the scalp anatomical region corresponding to a frontal lobe of the subject, and
        at least one parietal (P) EEG electrode located on the scalp anatomical region corresponding to a parietal lobe of the subject,
    determining from the response data, the level of modified state of consciousness of the subject,
    wherein the EEG data comprises data collected from the at least one F-EEG electrode, and the at least one P-EEG electrode, and the determining comprises:
        extracting from the at least one F-EEG electrode data, a power, F-power, associated with a band in a delta-theta, dt, frequency range; and
        extracting from the at least one P-EEG electrode data, a power, P-power, associated with a band in the delta-theta, dt, frequency range;
    wherein the dt frequency range encompasses both delta and theta brain waves; and
    wherein the F-power associated with a band in the dt frequency range and P-power associated with a band in the dt frequency range are indicative of the level of non-pharmacologically modified state of consciousness of the subject provided by the treatment session, and
    wherein a depth of dissociation, DoD, of the subject is determined from the F-power associated with a band in the dt frequency range, and the DoD is used to determine the level of non-pharmacologically modified state of consciousness of the subject.

2. The method according to claim 1, wherein:
    the F-power is associated with a frequency range greater than 0 Hz and equal to or less than 8 Hz, or a band within the aforementioned frequency range; and
    the P-power is associated with a frequency range greater than 0 Hz and equal to or less than 8 Hz, or a band within the aforementioned frequency range.

3. The method according to claim 1, wherein a reduction of said F-power associated with a band in the dt frequency range is indicative of a lowered level of non-pharmacologically modified state of consciousness of the subject.

4. The method according to claim 1, wherein the EEG data comprises data collected from the at least one F-EEG electrode and the determining comprises extracting from the F-EEG electrode data, a mean signal peak-to-peak amplitude, F-MSPA, wherein the F-MSPA is indicative of the level of non-pharmacologically modified state of consciousness of the subject.

5. The method according to claim 4, wherein a reduction of said F-MSPA is indicative of a lowered level of non-pharmacologically modified state of consciousness of the subject.

6. The method according to claim 1, wherein the level of modified state of consciousness is of a subject whose level of consciousness only will be/is being non-pharmacologically-modified.

7. The method according to claim 1, further comprising determining from the response data, a depth of state index, DoSI, the DoSI being a measure of the non-pharmacologically-modified state of consciousness of the subject.

8. The method according to claim 1, further comprising determining from the response data, a depth of hypnosis index, DoHI, the DoHI being a measure of the non-pharmacologically-modified state of consciousness of the subject.

9. The method according to claim 1, further comprising determining from the response data, a depth of dissociation index, DoDI, the DoDI being a measure of the non-pharmacologically-modified state of consciousness of the subject.

10. The method according to claim 1, for determining a level of sedation of a subject induced non-pharmacologically.

11. The method according to claim 1, further outputting to a graphical user interface, GUI, configured for indicating numerically and/or graphically one or more of:
  a current depth of at least one of:
    a state index, DoSI, the DoSI being a measure of the non-pharmacologically-modified state of consciousness of the subject,
    a hypnosis index, DoHI, the DoHI being a measure of the non-pharmacologically-modified state of consciousness of the subject, and
      a dissociation index, DoDI, the DoDI being a measure of the non-pharmacologically-modified state of consciousness of the subject;
    a current ratio between two of DoS(I), DoH(I), and DoD(I);
    trending (historical) of at least one of DoS(I), DoH(I), and DoD(I); and
    an expected value of at least one of DoS(I), DoH(I), and DoD(I).

12. The method according to claim 1, wherein the step of modifying the state of consciousness of the subject non-pharmacologically by presenting the treatment session to the subject, comprises presenting a treatment session containing hypnosis to the subject, providing the subject with a level of non-pharmacologically modified state of consciousness induced by hypnosis.

13. The method according claim 12, wherein the treatment session containing hypnosis is presented to the subject by playing through a media renderer.

14. The method according to claim 1, wherein the level of modified state of consciousness is of a subject whose level of consciousness will be/is being non-pharmacologically-modified and pharmacologically-modified.

15. The method according to claim 1, wherein the level of modified state of consciousness is determined in real time.

16. The method according to claim 1, wherein the depth of dissociation, DoD, of the subject is determined from:
  the F-power associated with a band in the dt frequency range, and
  the P-power associated with a band in the dt frequency range.

17. A system for determining and/or monitoring a level of consciousness of a subject receiving a treatment session, the system comprising:
  a monitoring apparatus configured to obtain response data comprising measured data of the subject during the treatment session;
  a controller module configured for receiving measured data from the monitoring apparatus,
  a media renderer configured for presenting the treatment session to the subject for non-pharmacologically modifying the level of consciousness of the subject,
  wherein the monitoring apparatus comprises, for obtaining measured data of the subject during the treatment session, one or more of:
    at least one frontal (F) EEG electrode configured for collection of F-EEG electrode data from a scalp anatomical region corresponding to a frontal lobe of the subject, and
    at least one parietal (P) EEG electrode configured for collection of P-EEG electrode data from a scalp anatomical region corresponding to a parietal lobe of the subject,
  wherein the controller module is configured to determine from the response data, the level of modified consciousness of the subject during the treatment session,
  wherein the system is configured to carry out a method for determining and/or monitoring a level of modified state of consciousness of a subject receiving a treatment session comprising modifying the state of consciousness of the subject non-pharmacologically, the method comprising the steps of:
    receiving response data being a subject's response to the treatment session, wherein the response data comprises measured data comprising electroencephalogram, EEG data, the EEG data comprising data collected from at least one of:
      the at least one frontal (F) EEG electrode configured to be located on the scalp anatomical region corresponding to a frontal lobe of the subject, and
      the at least one parietal (P) EEG electrode configured to be located on the scalp anatomical region corresponding to a parietal lobe of the subject,
    determining from the response data, the level of modified state of consciousness of the subject,
  wherein the EEG data comprises data collected from the at least one F-EEG electrode, and the at least one P-EEG electrode, and the determining comprises:
    extracting from the at least one F-EEG electrode data, a power, F-power, associated with a band in a delta-theta, dt, frequency range; and
    extracting from the at least one P-EEG electrode data, a power, P-power, associated with a band in the delta-theta, dt, frequency range;
  wherein the dt frequency range frequencies in a range encompassing both delta and theta brain waves;
  wherein the F-power associated with a band in the dt frequency range and P-power associated with a band in the dt frequency range are indicative of the level of non-pharmacologically modified state of consciousness of the subject; and
  wherein a depth of dissociation, DoD, of the subject is determined from the F-power associated with a band in the dt frequency range, and the DoD is used to determine the level of non-pharmacologically modified state of consciousness of the subject.

18. The system according to claim 17, wherein the media renderer is configured for presenting a treatment session containing hypnosis to the subject.

\* \* \* \* \*